US012707019B2

(12) United States Patent
Suzuki et al.

(10) Patent No.: US 12,707,019 B2
(45) Date of Patent: Aug. 11, 2026

(54) MEDICAL PROGRAM AND MEDICAL EXAMINATION SYSTEM

(71) Applicant: Kowa Company, Ltd., Nagoya (JP)

(72) Inventors: Takahiro Suzuki, Chofu (JP); Atsushi Kakuuchi, Chofu (JP)

(73) Assignee: Kowa Company, Ltd., Nagoya (JP)

( * ) Notice: Subject to any disclaimer, the term of this patent is extended or adjusted under 35 U.S.C. 154(b) by 106 days.

(21) Appl. No.: 18/569,580

(22) PCT Filed: Jun. 16, 2022

(86) PCT No.: PCT/JP2022/024128

§ 371 (c)(1),
(2) Date: Oct. 4, 2024

(87) PCT Pub. No.: WO2022/265064

PCT Pub. Date: Dec. 22, 2022

(65) Prior Publication Data

US 2025/0030814 A1 Jan. 23, 2025

(30) Foreign Application Priority Data

Jun. 17, 2021 (JP) ................................ 2021-101006
Sep. 22, 2021 (JP) ................................ 2021-154875

(51) Int. Cl.
*H04N 5/91* (2006.01)
*A61B 3/00* (2006.01)
(Continued)

(52) U.S. Cl.
CPC ............. *H04N 5/91* (2013.01); *A61B 3/0058* (2013.01); *A61B 3/145* (2013.01); *G06T 7/0012* (2013.01);
(Continued)

(58) Field of Classification Search
CPC .......... H04N 5/91; G16H 40/67; G16H 30/20; A61B 3/0058; A61B 3/145; G06T 7/0012;
(Continued)

(56) References Cited

U.S. PATENT DOCUMENTS 8,675,071 B1 * 3/2014 Slavin ................. G08B 25/001
348/143
2015/0257640 A1 9/2015 Graziano et al.
(Continued)

FOREIGN PATENT DOCUMENTS

JP 4136559 B2 6/2008
JP 2016207058 A 12/2016
(Continued)

OTHER PUBLICATIONS

International Search Report and Written Opinion (English Translation ISR only) for International Patent Application No. PCT/JP2022/024128 dated Aug. 30, 2022, pp. all.
(Continued)

*Primary Examiner* — Thai Q Tran
*Assistant Examiner* — Jose M Mesa
(74) *Attorney, Agent, or Firm* — Dorsey & Whitney LLP

(57) ABSTRACT

Provided is a non-statutory computer-readable medium storing thereon a medical program for implementing various kinds of processing in a terminal device used together with a medical examination device including an imaging camera, in order to play a video live and record the video, while maintaining usability of the medical examination device including the imaging camera, the video being generated by imaging by the medical examination device. The medical program, when executed, causes a processor of the terminal device to perform: playing video data live and displaying the video data on a display unit of the terminal device, the video
(Continued)

data being captured and simultaneously transmitted in real time by the medical examination device; and controlling start/stop of recording of the video data that is currently played live based on a predetermined operation.

20 Claims, 14 Drawing Sheets

(51) Int. Cl.
*A61B 3/14* (2006.01)
*G06T 7/00* (2017.01)
*G16H 30/20* (2018.01)
*G16H 40/67* (2018.01)

(52) U.S. Cl.
CPC ............ *G16H 30/20* (2018.01); *G16H 40/67* (2018.01); *G06T 2207/10016* (2013.01); *G06T 2207/30041* (2013.01); *G06T 2207/30168* (2013.01)

(58) Field of Classification Search
CPC . G06T 2207/10016; G06T 2207/30041; G06T 2207/30168
See application file for complete search history.

(56) References Cited

U.S. PATENT DOCUMENTS

2016/0338590 A1* 11/2016 Sagalovich ........ A61B 1/00066
2018/0027435 A1* 1/2018 Harrod .................. H04W 24/06 370/252
2018/0136486 A1* 5/2018 Macnamara ............. A61B 3/00
2018/0153399 A1 6/2018 Fink et al.
2019/0216440 A1* 7/2019 Kimoto .................. A61B 8/469
2020/0243195 A1 7/2020 Seriani
2021/0007606 A1* 1/2021 Su ........................ A61B 5/7278

FOREIGN PATENT DOCUMENTS

JP 2017041134 A 2/2017
JP 2018510384 A 4/2018
JP 2018143526 A 9/2018
KR 20170122981 A 11/2017
WO 2018148451 A1 8/2018
WO 2019087209 A1 5/2019
WO 2022265064 A1 12/2022

OTHER PUBLICATIONS

Extended European Search Report for EP Application No. 22825052.8, dated May 12, 2025, pp. all.
Estrada, et al., "Enhanced video indirect ophthalmoscopy (VIO) via robust mosaicing", Biomedical Optics Express, vol. 2, No. 10, Sep. 29, 2011, p. 2871, pp. all.
Office Action for Taiwanese Patent Application No. 111122421, dated Sep. 8, 2025, pp. all.
Notice of Reasons for Refusal for Japanese Patent Application No. 2023-530402 dated on Feb. 24, 2026, pp. all.
The First Office Action for Chinese Patent Application No. 202280042725.X, dated May 1, 2026, pp. all.

* cited by examiner

MEDICAL PROGRAM AND MEDICAL EXAMINATION SYSTEM

CROSS-REFERENCE TO RELATED APPLICATION(S)

This application is a continuation of PCT Application No. PCT/JP2022/024128 filed Jun. 16, 2022, which claims priority to Japanese Application No. 2021-101006 filed on Jun. 17, 2021, and No. 2021-154875 filed on Sep. 22, 2021, which are incorporated herein by reference, in their entirety, for any purpose.

TECHNICAL FIELD

The present invention relates to a medical program and a medical examination system used for an examination of an object for examination.

BACKGROUND ART

Conventionally, a medical examination device that images an object for examination to examine the object for examination has been used. For example, Patent Literature 1 discloses a medical examination device that generates imaging data by imaging an object for examination and records the generated data in a predetermined recording means.

CITATION LIST

Patent Literature

Patent Literature 1: JP 4136559

SUMMARY OF INVENTION

Technical Problem

The medical examination device disclosed in Patent Literature 1 can record a plurality of pieces of imaging data generated by imaging of the object for examination in the recording means included in the medical examination device. However, when a configuration of recording a video is employed in the medical examination device, the usability of the medical examination device may be impaired. For example, the medical examination device needs to have a storage function, which may raise a problem of an increase in size of the medical examination device. In addition, when, for example, information cannot be written in recorded data in the medical examination device, and the medical examination device images and records data of a plurality of subjects and then transmits the data to another terminal, there is a possibility that the data of a wrong subject may be transmitted.

The present invention has been made in view of the above problems, and an object of the present invention is to provide a medical program and a medical examination system with which it is possible to record video data generated by imaging by a medical examination device provided with an imaging camera while maintaining usability of the medical examination device.

Solution to Problem

A medical program according to the present invention is a medical program for implementing various kinds of processing in a terminal device used together with a medical examination device including an imaging camera, the medical program implementing: a reception function of receiving various types of data including video data (hereinafter referred to as real-time video data) that is captured and simultaneously transmitted in real time by the medical examination device; a display control function of playing a video live and displaying the video on a display unit included in the terminal device, the video being indicated by the real-time video data that has been received; a video recording function of controlling start/stop of recording of the real-time video data that is currently played live on the basis of a predetermined operation on the terminal device; and a recording control function of recording the real-time video data during a period from when recording is started to when the recording is stopped by the video recording function into a recording means included in the terminal device as recorded video data.

In addition, in the medical program according to the present invention, the display control function may implement a function of displaying a first button for instructing the start/stop of the recording of the real-time video data that is currently played live on the display unit that is a touch panel included in the terminal device, and the video recording function may implement a function of controlling the start/stop of the recording of the real-time video data that is currently played live on the basis of an input operation on the first button.

In addition, in the medical program according to the present invention, the reception function may implement a function of receiving, from the medical examination device, information indicating a control request for the start/stop of the recording of the real-time video data based on an operation on a predetermined operation unit physically provided in the medical examination device, and the video recording function may implement a function of controlling the start/stop of the recording of the real-time video data that is currently played live on the basis of the information indicating the control request received from the medical examination device.

In addition, in the medical program according to the present invention, the display control function may implement a function of displaying, on the display unit, a second button for accepting an input operation of inputting an extraction request for extracting still image data from the recorded video data when the recorded video data is played and displayed on the display unit, and the recording control function may implement a function of recording still image data corresponding to a still image displayed on the display unit in the recording means when the input operation on the second button is performed.

In addition, the medical program according to the present invention may further implement an acceptance function of accepting an input operation of inputting identification information for identifying an object for examination, wherein the recording control function may implement a function of recording the real-time video data in the recording means as the recorded video data only when the input operation of inputting the identification information is accepted.

In addition, in the medical program according to the present invention, the recording control function may implement a function of recording the real-time video data in the recording means as the recorded video data in association with the identification information input by the input operation that has been accepted.

In addition, the medical program according to the present invention may further implement an acceptance function of accepting an input operation of inputting identification information for identifying an object for examination, wherein the display control function may implement a function of playing the video live and displaying the video on the display unit only when the input operation of inputting the identification information is accepted, the video being indicated by the real-time video data that has been received.

In addition, in the medical program according to the present invention, the display control function may implement a function of, when the video indicated by the real-time video data is displayed, displaying the identification information indicating an object for examination on the display unit along with the video.

In addition, in the medical program according to the present invention, the medical examination device may be used to examine an eye of a subject, the display control function may implement a function of displaying, on the display unit, a third button for selecting the left eye or the right eye of the subject as an object for examination, and the recording control function may implement a function of recording, in the recording means, the real-time video data as the recorded video data in association with information regarding selection of the left eye or the right eye of the subject on the basis of a selecting operation on the third button.

In addition, in the medical program according to the present invention, the display control function may implement a function of, when the video indicated by the recorded video data is displayed, displaying the information regarding selection of the left eye or the right eye of the subject on the display unit in association with the video.

In addition, the medical program according to the present invention may further implement: a transmission function of transmitting the recorded video data to a predetermined server device; and a communication control function of performing control so that, while one of communication for receiving the real-time video data by the reception function and communication for transmitting the recorded video data by the transmission function is performed, the other communication is inhibited.

A medical examination system according to the present invention is a medical examination system comprising: a medical examination device provided with an imaging camera; a terminal device; and a server device, wherein the medical examination device transmits video data generated by imaging an object for examination to the terminal device in real time, and the terminal device includes a reception unit that receives various types of data including video data (hereinafter referred to as real-time video data) that is captured and simultaneously transmitted in real time by the medical examination device, a display control unit that plays a video live and displays the video on a display unit included in the terminal device, the video being indicated by the real-time video data that has been received, a video recording unit that controls start/stop of recording of the real-time video data that is currently played live on the basis of a predetermined operation on the terminal device, a recording control unit that records the real-time video data during a period from when recording is started to when the recording is stopped by the video recording unit into a recording means included in the terminal device as recorded video data, and a transmission unit that transmits the recorded video data to the server device.

In addition, in the medical examination system according to the present invention, the server device may classify and manage the recorded video data received from the terminal device on the basis of identification information that is information for identifying the object for examination and that is associated by the terminal device.

In addition, in the medical examination system according to the present invention, the medical examination device may function as one access point, and disable communication connection with another device when establishing communication connection with the terminal device.

An image processing program according to the present invention is an image processing program for causing a computer to implement a function relating to image processing, the program causing the computer to implement: a video data acquiring function of acquiring video data to be processed; a focus level calculating function of calculating focus levels of a part of or all of frames constituting the video data; a still image extracting function of extracting, as extraction still image data, a part of or all of frames (hereinafter referred to as candidate frames) having focus levels equal to or greater than a predetermined value among the frames whose focus levels have been calculated; and a recording function of recording the extraction still image data in a recording means included in the computer.

In addition, in the image processing program according to the present invention, the still image extracting function may include excluding a predetermined number of the candidate frames from frames to be extracted in descending order of the focus level, when the candidate frames are arranged in chronological order and there is a plurality of the candidate frames within a preset time range.

In addition, in the image processing program according to the present invention, the still image extracting function may include, when there is the candidate frame having the focus level smaller than that of a frame of interest within the predetermined time range from a time point of the frame of interest while the candidate frames are sequentially focused in chronological order during extraction of the extraction still image data from the candidate frames, excluding the candidate frame from the frames to be extracted.

In addition, in the image processing program according to the present invention, the still image extracting function may include excluding a frame having the focus level that is minimum among the candidate frames from frames to be extracted so that a total number of the extraction still image data does not exceed a predetermined upper limit number, when the extraction still image data is extracted from the candidate frames.

In addition, in the image processing program according to the present invention, the calculation of the focus level by the focus level calculating function may be achieved by edge extraction image generating processing for generating an edge extraction image by execution of edge extraction processing on the frame, and calculation processing of calculating the focus level of a frame corresponding to the edge extraction image on the basis of edge distribution in the edge extraction image.

In addition, in the image processing program according to the present invention, the focus level calculating function may include executing green component image generating processing of extracting a green component from color information of each pixel constituting the frame to generate green component image data, and grayscale processing of converting the green component image data into grayscale to generate grayscale image data, and calculating the focus level on the basis of the grayscale image data obtained by the grayscale processing.

In addition, in the image processing program according to the present invention, the focus level calculating function may include executing adjustment processing of adjusting a black level of the grayscale image data, and calculating the focus level on the basis of the grayscale image data which has been adjusted in black level by the adjustment processing.

In addition, in the image processing program according to the present invention, the focus level calculating function may include setting one frame as a target frame whose focus level is to be calculated among the frames constituting the video data at predetermined time intervals or every predetermined number of frames.

In addition, in the image processing program according to the present invention, the video data may be data of a video obtained by imaging an eye of a subject, and the focus level calculating function may include calculating the focus level of a region obtained by excluding a region of a predetermined range on an upper side and/or a lower side of the frame.

In addition, in the image processing program according to the present invention, the video data acquiring function may include storing the video data that has been acquired in a storage means included in the computer, the program causing the computer to implement a deleting function of deleting the video data that has been stored in the storage means at a predetermined timing after the extraction still image data is extracted by the still image extracting function.

In addition, the image processing program according to the present invention may cause the computer to implement: a display control function of displaying an extraction still image indicated by the extraction still image data on a display unit included in the computer; and an acceptance function of accepting, from a user, a selecting operation on the extraction still image that has been displayed, wherein the recording function may include a function of recording, in the recording means, the extraction still image data that indicates the extraction still image selected by the selecting operation that has been accepted.

In addition, in the image processing program according to the present invention, the display control function may implement a function of displaying a video indicated by the video data including the extraction still image on the display unit when a predetermined first input operation is performed, the acceptance function may implement a function of accepting a selecting operation of selecting the frame of the video being displayed, and the recording function may implement a function of recording, in the recording means, still image data indicating the frame selected by the selecting operation which has been accepted.

In addition, in the image processing program according to the present invention, the display control function may include continuing to play the video data from the extraction still image data when a predetermined second input operation is performed on any of extraction still images indicated by the extraction still image data.

Advantageous Effects of Invention

The present invention can provide a medical program and a medical examination system with which it is possible to record video data generated by imaging by a medical examination device provided with an imaging camera while maintaining usability of the medical examination device.

The present invention can also provide an image processing program with which it is possible to automatically extract and record still image data from video data.

DESCRIPTION OF EMBODIMENTS

First Embodiment

Figure 1:
FIG. 1 is an explanatory diagram for describing an example of the configuration of a medical examination system 100 corresponding to at least one embodiment of the present invention.
Figure 1:
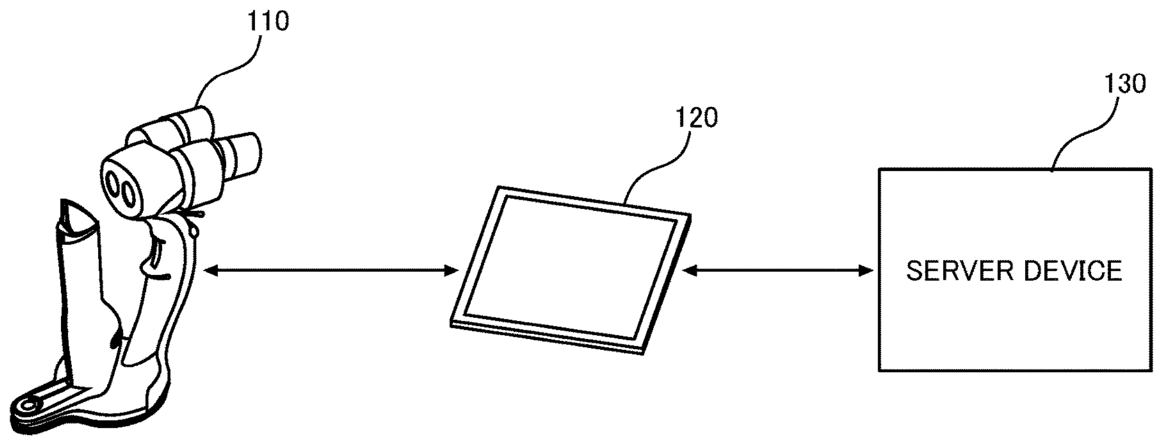

An example of a medical examination system 100 according to an embodiment of the present invention will be described below with reference to the drawings. FIG. 1 is an explanatory diagram for describing an example of the configuration of the medical examination system 100 corresponding to at least one embodiment of the present invention. As illustrated in FIG. 1, the medical examination system 100 according to the embodiment of the present invention includes a medical examination device 110, a terminal device 120, and a server device 130.

The medical examination device 110 is a device for examining an object for examination. The object for examination is, for example, a human or an animal. The medical examination device 110 includes at least an imaging camera and has a function of imaging the object for examination. The medical examination device 110 also has a communication function, and performs wireless communication with the terminal device 120 in the present embodiment. Note that, in a case where the medical examination device 110 performs wired communication with the terminal device 120, the medical examination device 110 and the terminal device 120 are connected by, for example, a universal serial bus (USB) cable or the like.

The medical examination device 110 images the object for examination and simultaneously transmits video data to the terminal device 120 in real time. Here, imaging and simultaneously transmitting the video data in real time means directly transmitting the captured video data to the terminal device 120 without causing a time lag. Hereinafter, video data captured and simultaneously transmitted in real time is referred to as "real-time video data".

In the present embodiment, the medical examination device 110 is a handheld device called a slit lamp that irradiates an eye (hereinafter referred to as subject's eye) of a subject with slit light and observes scattered light generated by scattering in the subject's eye, thereby inspecting the cornea, the crystalline lens, or the like of the subject's eye. Note that the medical examination device 110 is not limited to such an example, and may be various medical devices including a handheld medical examination device such as a handheld fundus camera and a stationary medical device such as a testing device for dry eyes, in addition to the handheld slit lamp.

Note that the medical examination device 110 may function as one wireless local area network (LAN) access point, and may be connectable to only one device for simultaneous communication. For example, when establishing a communication connection with the terminal device 120, the medical examination device 110 disables a communication connection with another device. Such communication control can prevent a situation in which an unintended device receives video data and displays a video indicated by the video data at the time of executing imaging during inspection, and as a result, personal information can be protected. In addition, such a communication control method allows the medical examination device 110 not to have information for selecting a communication partner. This is because, unlike a method for implementing one-to-one communication using, for example, the same ID attached to a transmission/reception signal between devices, the communication control method described above is on a first-come-first-served basis in which a device that first establishes communication (for example, establishes a WiFi (registered trademark) connection) with the medical examination device 110 can communicate with the medical examination device 110.

The terminal device 120 is a device used together with the medical examination device 110. In the present embodiment, the terminal device 120 is a tablet terminal including a touch panel.

The terminal device 120 may be a device designed as a dedicated machine, but can be implemented by a general computer. That is, the terminal device 120 includes at least a central processing unit (CPU) that would be commonly included in a general computer and a memory. Processing in the terminal device 120 is implemented by reading a program for executing the processing from a memory and executing the program in a CPU or a graphics processing unit (GPU (image processing device)) that functions as a control circuit (processing circuit, processing circuitry). In other words, the processor (processing circuit) is configured to be able to execute the processing of each device by executing the program. Hereinafter, any device is applicable as the terminal device 120 as long as it can execute processing equivalent to that of a computer, and the terminal device 120 can also be implemented by, for example, a smartphone, a tablet terminal, or the like. In the present embodiment, the terminal device 120 is a tablet terminal as described above.

The terminal device 120 has a function of communicating with the medical examination device 110 and the server device 130. Specifically, the terminal device 120 performs wireless communication with the medical examination device 110 and performs wired or wireless communication with the server device 130 to transmit and receive various types of information. More specifically, the terminal device 120 receives the real-time video data transmitted from the medical examination device 110, and records the data in a recording means (hereinafter referred to as a terminal-side recording means) included in the terminal device. Then, the terminal device 120 transmits the recorded real-time video data (hereinafter also referred to as recorded video data) to the server device 130. Note that, in a case where the terminal device 120 performs wired communication with the server device 130, the terminal device 120 and the server device 130 are connected by, for example, a USB cable or the like.

Furthermore, the terminal device 120 includes a display unit (hereinafter referred to as a terminal display unit), and displays various types of information by the terminal display unit. Specifically, the terminal device 120 displays a video indicated by the real-time video data received from the medical examination device 110 and a video indicated by the recorded video data recorded in the terminal-side recording means on the terminal display unit. In the present embodiment, the terminal device 120 which is a tablet terminal includes a touch panel functioning as the terminal display unit, displays various types of information including a video indicated by the real-time video data, a video indicated by the recorded video data, and the like on the touch panel, and accepts various input operations from a user by a touch operation on the touch panel.

The server device 130 manages various types of information such as video data transmitted from the terminal device 120. The server device 130 includes a recording means that records recorded video data and still image data received from the terminal device 120. The recorded video data to be recorded in the recording means may be classified and managed on the basis of identification information associated by the terminal device 120 (attached at the time of recording by the terminal device 120). In the present embodiment, the server device 130 records the recorded video data in the recording means included in the server device 130 in association with the electronic medical record corresponding to a subject on the basis of the identification information associated by the terminal device 120. Note that the recording means for recording the recorded video data transmitted from the terminal device 120 is not particularly limited as long as it is different from the terminal-side recording means. Another example of the recording means that records the recorded video data transmitted from the terminal device 120 includes a recording means belonging to the same network as the server device 130.

Communication between the server device 130 and the terminal device 120 may be established by wired connection using, for example, a USB cable, or may be established by wireless communication such as using a wireless LAN. Note that the server device 130 is, for example, a device that manages electronic medical records or the like installed in an in-hospital LAN of a hospital.

Figure 2:
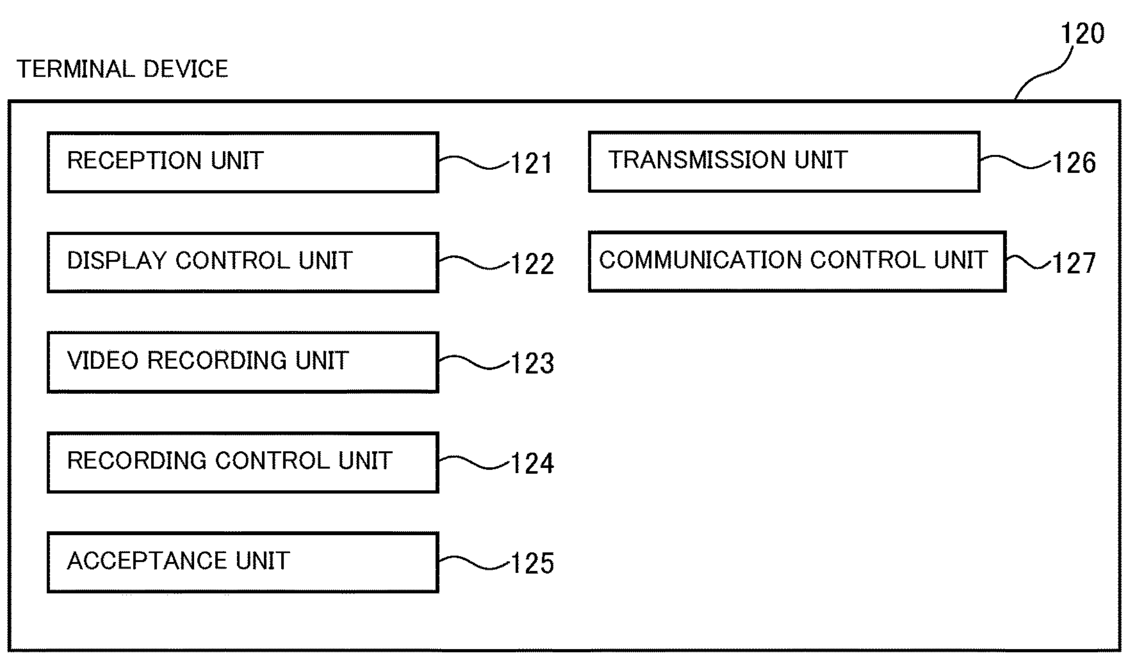
FIG. 2 is a block diagram illustrating an example of the functional configuration of a terminal device 120 corresponding to at least one embodiment of the present invention.

FIG. 2 is a block diagram illustrating an example of the functional configuration of the terminal device 120 corresponding to at least one embodiment of the present invention.

As illustrated in FIG. 2, the terminal device 120 includes a reception unit 121, a display control unit 122, a video recording unit 123, a recording control unit 124, an acceptance unit 125, a transmission unit 126, and a communication control unit 127. First, an outline of a functional configuration example of the terminal device 120 will be described.

The reception unit 121 has a function of receiving various kinds of data including video data (real-time video data) captured by the medical examination device 110 and simultaneously transmitted in real time.

Furthermore, the reception unit 121 may receive, from the medical examination device 110, information indicating a control request for starting/stopping recording of real-time video data in the terminal-side recording means based on an operation on a predetermined operation unit physically provided in the medical examination device 110. Here, the operation unit is, for example, a button or a dial switch. The information indicating the control request for starting/stopping recording is not particularly limited, but is preferably information regarding contents shared between the medical examination device 110 and the terminal device 120 in advance.

The display control unit 122 has a function of playing a video live and displaying the video in the terminal display unit, the video being indicated by the received real-time video data. Specifically, the display control unit 122 has a function of displaying a video indicated by the real-time video data in the terminal display unit, the moment the reception unit 121 receives the real-time video data. Due to the video being played live and displayed as described above, the user can perform the imaging operation while confirming the situation of the imaging by the medical examination device 110.

The video recording unit 123 has a function of controlling start/stop of the recording of the real-time video data which is currently played live on the basis of a predetermined operation on the terminal device 120. Here, controlling start/stop of recording of the real-time video data which is currently played live means starting recording of the real-time video data into the terminal-side recording means on the basis of a predetermined operation as a trigger for starting recording and stopping the recording of the real-time video data into the terminal-side recording means on the basis of a predetermined operation as a trigger for ending the recording. Examples of the predetermined operation include an input operation on a recording start button and a stop button which are displayed on the terminal display unit, and an operation on an operation unit that functions as a recording start button and a stop button physically provided on the terminal device 120. The start/stop of recording is managed by, for example, a predetermined flag. Note that the video recording unit 123 may control start/stop of recording of the real-time video data which is currently played live on the basis of the information indicating the control request from the medical examination device 110 received by the reception unit 121.

The recording control unit 124 has a function of recording the real-time video data from the start to the stop of recording by the video recording unit 123 in the terminal-side recording means as recorded video data. Here, the configuration for recording the real-time video data in the terminal-side recording means as the recorded video data is not particularly limited, but a configuration for recording the real-time video data in association with predetermined information is preferable. Examples of the predetermined information include identification information for uniquely identifying the object for examination and an imaging date and time by the medical examination device 110. The identification information here is not particularly limited as long as it can identify the object for examination.

The acceptance unit 125 has a function of accepting an operation of inputting identification information for identifying an object for examination. The identification information acquired by the acceptance unit 125 is recorded in association with the recorded video data recorded by the recording control unit 124. Here, examples of the input operation that can be used include, in addition to an input using a software key displayed on the terminal display unit, an input using a hardware key (physical key) in a case where the terminal device 120 is provided with the hardware key, an input by voice in a case where the terminal device 120 has a microphone function, and a method of inputting the identification information by reading a one-dimensional/two-dimensional barcode representing the identification information by a barcode reader function or a camera function in a case where the terminal device 120 has the barcode reader function or the camera function. Furthermore, in the input operation, in a case where the terminal device 120 has a camera function, an input by reading identification information on a card captured by the terminal device 120 by an optical character recognition (OCR) technology may be used. It is obvious that the above methods may be used in combination. The display control unit 122 may play the video live and display the video on the terminal display unit only when the operation of inputting the identification information is accepted, the video being indicated by the received real-time video data. Furthermore, the display control unit 122 may display the identification information together on the terminal display unit when displaying the video indicated by the real-time video data. Then, the recording control unit 124 may record the real-time video data in the terminal-side recording means as the recorded video data only when the operation of inputting the identification information is accepted. Here, the recording control unit 124 may record the real-time video data in the terminal-side recording means as the recorded video data in association with the identification information input by the input operation that has been accepted. Such a configuration facilitates management of recorded video data.

The transmission unit 126 has a function of transmitting the recorded video data to a predetermined server device. The predetermined server device corresponds to the server device 130 in FIG. 1. Here, the recorded video data to be transmitted to the server device 130 is determined by, for example, a selecting operation by the user. Hereinafter, the recorded video data transmitted to the server device 130 is referred to as "server management video data". The server device 130 records the received server management video data in a recording means included in the server device 130 or a recording means included in another device belonging to a network same as the network of the server device 130.

The communication control unit 127 has a function of performing control so as to inhibit one of communication for receiving the real-time video data by the reception unit 121 and communication for transmitting the recorded video data by the transmission unit 126 while the other communication is being performed. For example, the communication control unit 127 inhibits the communication for transmitting the recorded video data by the transmission unit 126 during communication for receiving the real-time video data by the reception unit 121. Here, the communication for receiving the real-time video data by the reception unit 121 may be regarded as being continued until the reception of the data is stopped by the reception unit 121 due to the transmission of the real-time video data from the medical examination device 110 being stopped.

In the following, a configuration for controlling a graphical user interface (GUI) displayed on the terminal display unit of the terminal device 120 by the display control unit 122 will be described.

The display control unit 122 may display, on the terminal display unit which is a touch panel included in the terminal device 120, a first button for instructing start/stop of recording of the real-time video data which is currently played live into the terminal-side recording means. The video recording unit 123 may control start/stop of recording of the real-time video data which is currently played live on the basis of an input operation on the first button. For example, in a case where the first button displayed on the touch panel is touched, processing of controlling start/stop of recording of the real-time video data which is currently played live may be executed. The display mode of the first button is not particularly limited, but a mode by which the user can recognize that the first button relates to the processing of controlling start/stop of the recording is preferable.

Further, the display control unit 122 may display, on the terminal display unit, a second button for accepting an operation of inputting an extraction request for extracting still image data from the recorded video data when the recorded video data is played and displayed on the terminal display unit. The input operation here is, for example, a touch operation. The display mode of the second button is not particularly limited, but a mode by which the user can recognize that the second button relates to the request to extract a still image is preferable. Then, the recording control unit 124 may record, into the terminal-side recording means, still image data corresponding to the still image displayed on the terminal display unit when the input operation on the second button is performed. With such a configuration, it is possible to easily extract a still image from a video when the still image is needed. Note that the still image data recorded into the terminal-side recording means may be transmitted to a predetermined server device (for example, server device 130) by the transmission unit 126.

In addition, when the medical examination device 110 is a device for inspecting the subject's eyes, the display control unit 122 may display, on the terminal display unit, a third button for selecting either the left eye or the right eye of the subject as the object to be inspected. The display mode of the third button is not particularly limited, but a mode by which the user can recognize that the third button relates to selecting either the left eye or the right eye of the subject as the object to be inspected is preferable.

Then, when recording the real-time video data as the recorded video data, the recording control unit 124 may record, in the terminal-side recording means, information regarding the selection of the left eye or the right eye of the subject determined on the basis of the selecting operation on the third button in association with the recorded video data. With such a configuration, for example, it is not necessary to organize the data later with respect to whether the data corresponds to the left eye or the right eye, whereby the data management is facilitated.

Furthermore, when displaying the video indicated by the recorded video data, the display control unit 122 may display, on the terminal display unit, the information regarding the selection of the left eye or the right eye in association with the video. Examples of the information regarding the selection of the left eye or the right eye include character information and icons indicating the left eye or the right eye. With such a configuration, the user can confirm which one of the left eye and the right eye is currently selected and can easily confirm whether or not the information regarding the selection of the left eye or the right eye is correct.

Note that the display control unit 122 may perform processing of changing a playback range and a playback method of a video indicated by the displayed recorded video data on the basis of a predetermined operation, such as an operation for enlarging the video, when the video is played. Here, the predetermined operation means a predetermined type of operation on a predetermined place on the terminal display unit. Examples of the predetermined operation include touch, drag, pinch out, pinch in, long press, and slide. Furthermore, examples of the processing for changing the playback range and the playback method of the video include processing of changing the playback range to the display range of a still image in one frame of the video and adjustment of the display time of the video (adjustment of a frame to be displayed among a plurality of frames of the video). For example, when playing and displaying the recorded video data on the terminal display unit, the display control unit 122 may enlarge/reduce the video on the basis of the predetermined operation to change the display range and display the video. In addition, the recording control unit 124 may further record a video displayed with the display range being changed by the display control unit 122. Further, when the processing of changing the playback range or the playback method of the video is performed, the recording control unit 124 may record, in the terminal-side recording means, still image data corresponding to the still image in the video displayed on the terminal display unit when the input operation on the second button is performed. For example, when the input operation on the second button is performed while the video is displayed with the display range being changed on the basis of the display control unit 122, the recording control unit 124 may record, in the terminal-side recording means, still image data corresponding to the still image with the display range displayed on the terminal display unit. When an input operation is performed on the second button in a case where the video indicated by the recorded video data is enlarged and displayed, the enlarged still image displayed when the input operation is performed on the second button is recorded in the terminal-side recording means.

In addition, the terminal device 120 may be configured to execute processing of editing the recorded video data. For example, the display control unit 122 may execute display for facilitating deletion of unnecessary frames by displaying consecutive frames of video data in time series.

Figure 3:
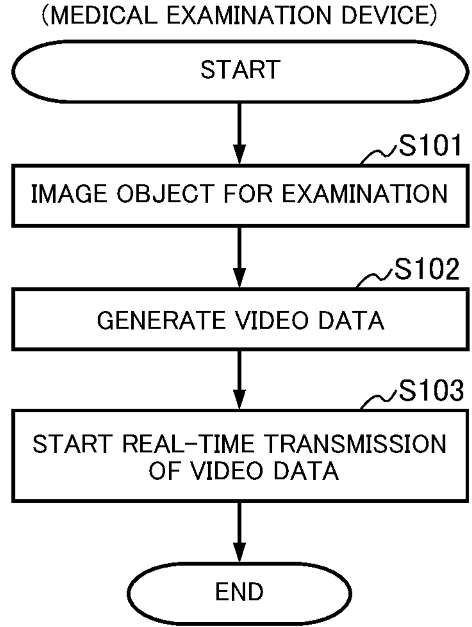
FIG. 3 is a flowchart illustrating an example of a flow of processing performed by a medical examination device 10 corresponding to at least one embodiment of the present invention.

FIG. 3 is a flowchart illustrating an example of a flow of operation performed by the medical examination device 110 corresponding to at least one embodiment of the present invention.

In FIG. 3, the operation performed by the medical examination device 110 is started by imaging the object for examination (step S101). Next, the medical examination device 110 generates video data by imaging the object for examination (step S102). Here, the processing of generating the video data is executed in parallel with the process of step S101. Next, the medical examination device 110 starts real-time transmission of the generated video data to the terminal device 120 (step S103). In the present embodiment, the transmission of the video data by the medical examination device 110 is continued after step S103.

Figure 4:
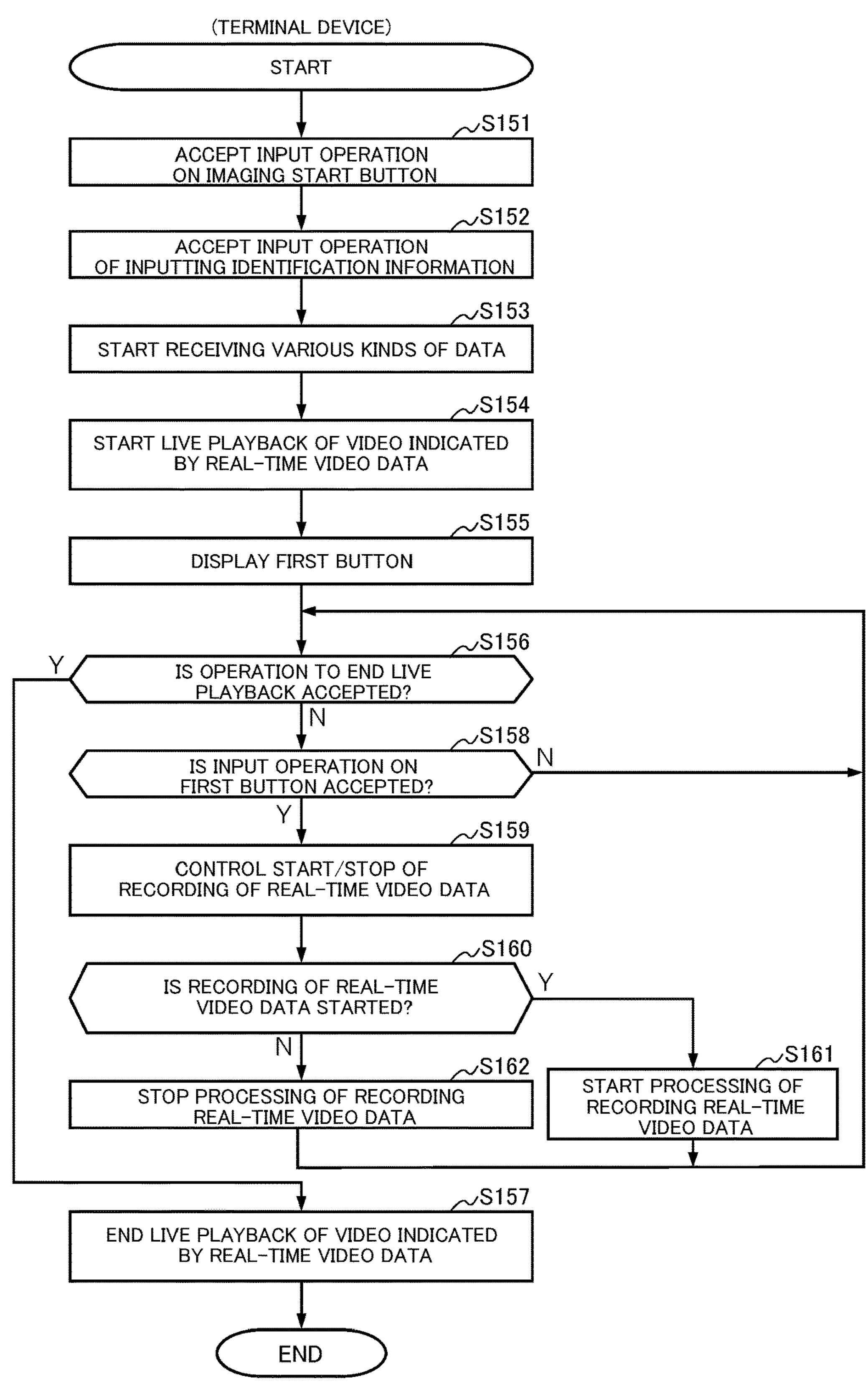
FIG. 4 is a flowchart illustrating an example of a flow of processing performed by the terminal device 120 corresponding to at least one embodiment of the present invention.

FIG. 4 is a flowchart illustrating an example of a flow of processing performed by the terminal device 120 corresponding to at least one embodiment of the present invention.

In FIG. 4, the operation by the terminal device 120 is started in response to an input operation on an imaging start button displayed on the terminal display unit after the communication connection with the medical examination device 110 is established (step S151). Next, the terminal device 120 accepts an input operation of inputting identification information (step S152). In this example, the terminal device 120 accepts the input operation using a software key displayed on the terminal display unit. Next, upon accepting the input operation of inputting the identification information in step S152, the terminal device 120 starts receiving various kinds of data including the real-time video data captured by the medical examination device 110 (step S153). Next, the terminal device 120 starts live playback and display of the video indicated by the real-time video data on the terminal display unit (step S154). Note that, although this flowchart has described the configuration in which the live playback of the real-time video data is started after the input of the identification information, the configuration of the medical examination system is not necessarily limited thereto. The live playback may be started when the communication connection between the medical examination device 110 and the terminal device 120 is established.

Next, the terminal device 120 displays, on the terminal display unit which is a touch panel, a first button for instructing start/stop of recording of the real-time video data which is currently played live into the terminal-side recording means (step S155). In the present embodiment, the terminal device 120 displays a recording control button as the first button on the display screen of the terminal display unit in a region below the video indicated by the real-time video data which is currently played live. The recording control button here is a toggle button that serves as both a button for starting recording and a button for stopping recording.

Next, in a case where the operation to end the live playback of the video indicated by the real-time video data is accepted by the terminal device 120 (Y in step S156), the terminal device 120 ends the live playback of the video indicated by the real-time video data (step S157), and the terminal device 120 ends the operation. In the present embodiment, in a case where a touch operation on the button for returning to a start screen from a live playback screen displayed on the touch panel of the terminal device 120 is accepted, the live playback of the video indicated by the real-time video data ends.

On the other hand, when the terminal device 120 has not accepted the operation to end the live playback of the video indicated by the real-time video data (N in step S156) and when the terminal device 120 has not accepted the input operation on the first button (N in step S158), the processing returns to the determination in step S156.

On the other hand, when the terminal device 120 has not accepted the operation to end the live playback of the video indicated by the real-time video data (N in step S156) and when the terminal device 120 has accepted the input operation on the first button (Y in step S158), the terminal device 120 controls start/stop of recording of the real-time video data that is currently played live (step S159). In the present embodiment, control is performed such that recording is started in a case where recording is not started when a touch operation on the recording control button is accepted, and recording is stopped in a case where recording is started. Note that the present embodiment is configured such that, in a case where the input operation on the first button is first accepted after the live playback of the video indicated by the real-time video data is started, recording of the video data is started.

Next, in a case where recording of the real-time video data that is currently played live is started in step S159 (Y in step S160), the terminal device 120 starts processing of recording the real-time video data in the terminal-side recording means as recorded video data (step S161), and returns to the determination in step S156.

On the other hand, in a case where recording of the real-time video data that is currently live is stopped in step S159 (N in step S160), the terminal device 120 stops the processing of recording the real-time video data in the terminal-side recording means as recorded video data (step S162), and returns to the determination in step S156.

An example of the flow of processing performed by the medical examination device 110 and the terminal device 120 has been described above.

FIGS. 5 to 9 are explanatory diagrams illustrating an example of the display screen of the terminal device 120 corresponding to at least one embodiment of the present invention.

Figure 5:
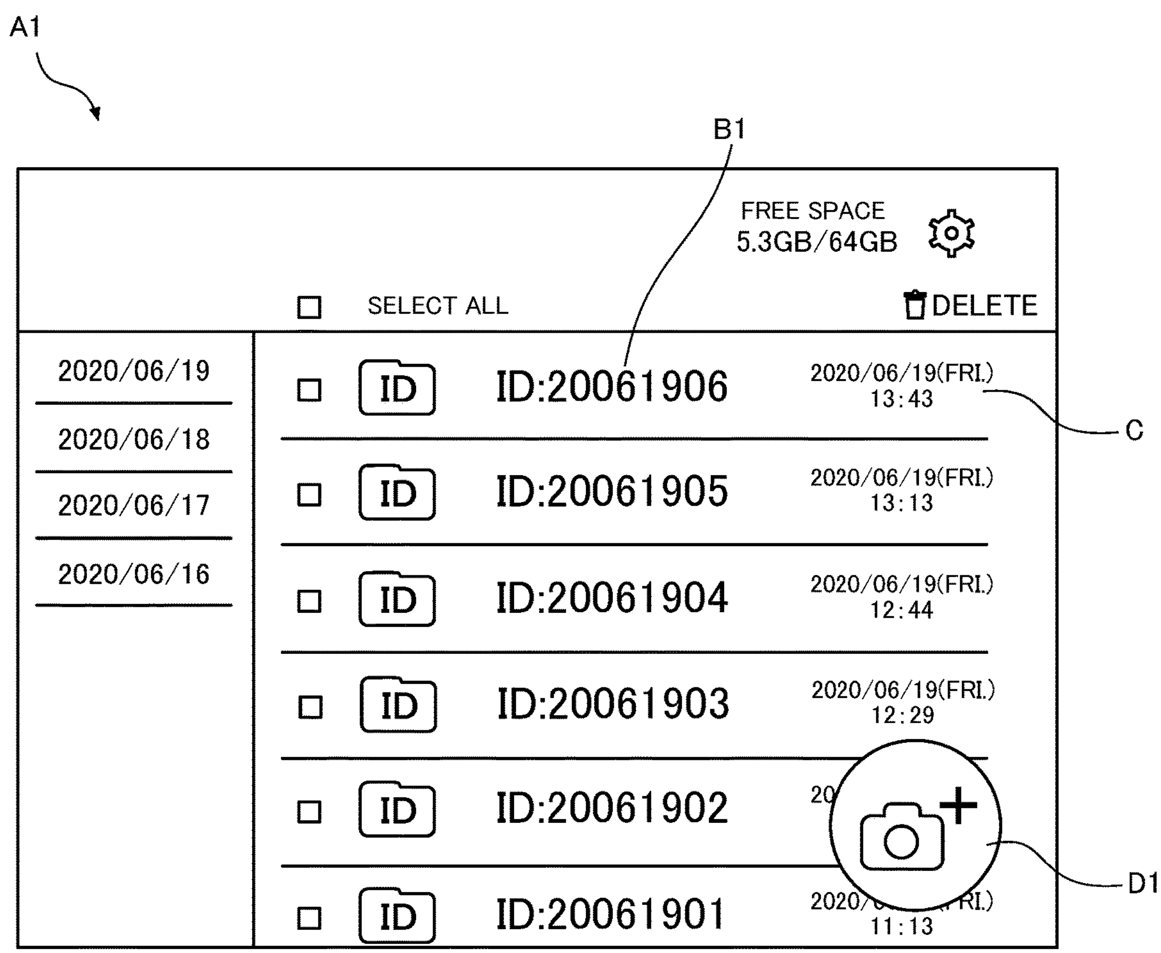
FIG. 5 is an explanatory diagram illustrating an example of a display screen of the terminal device 120 corresponding to at least one embodiment of the present invention.

FIG. 5 is a diagram illustrating an example of the display screen of the terminal device 120 in a case where a medical application is activated on the terminal device 120. FIG. 5 illustrates a display screen A1 which is a start screen of the medical application. The display screen A1 which is a screen immediately after activation of the medical application displays a list of the identification information pieces of subjects for which the recorded video data is recorded in the terminal-side recording means of the terminal device 120.

The present application can execute an operation of recording video data of a subject imaged by the imaging camera included in the medical examination device 110 as recorded video data, manages the recorded video data by dividing the same into folders for each of management subject identification information B1, and displays inspection date and time information (inspection start date and time information) C and an imaging start button D1 on the display screen A1. The inspection date and time information C is information indicating the inspection date and time corresponding to each management subject identification information B1. The imaging start button D1 is a button for playing the video live and displaying the video on the terminal display unit, the video being indicated by the real-time video data. Note that, on the basis of a selecting operation on at least one folder in the display screen A1, recorded video data or still image data stored into the folder may be transferred to the server device 130.

Figure 6A:
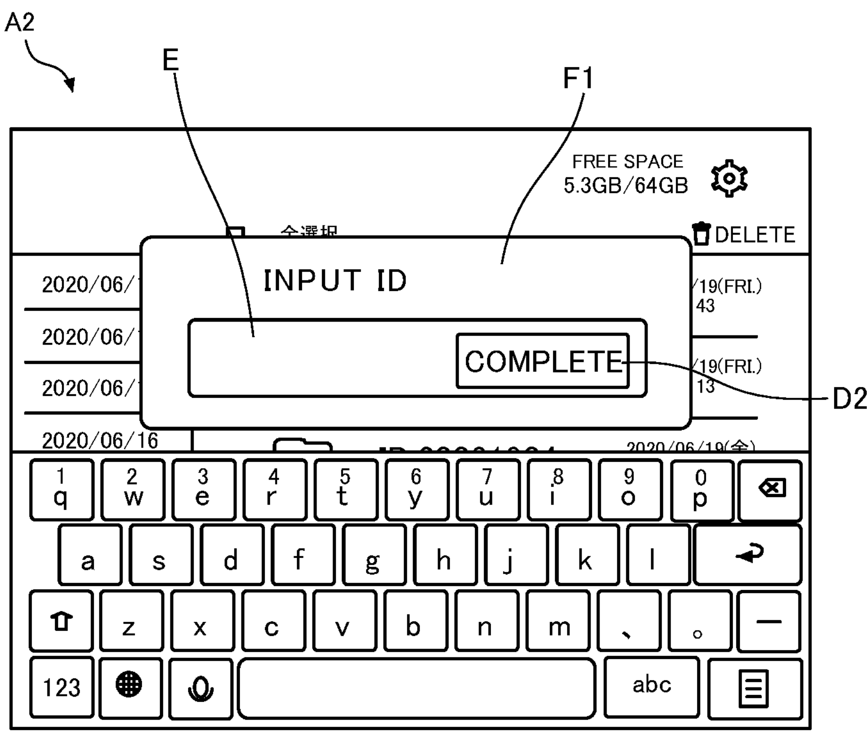
FIGS. 6A and 6B are explanatory diagrams illustrating an example of the display screen of the terminal device 120 corresponding to at least one embodiment of the present invention.
Figure 6B:
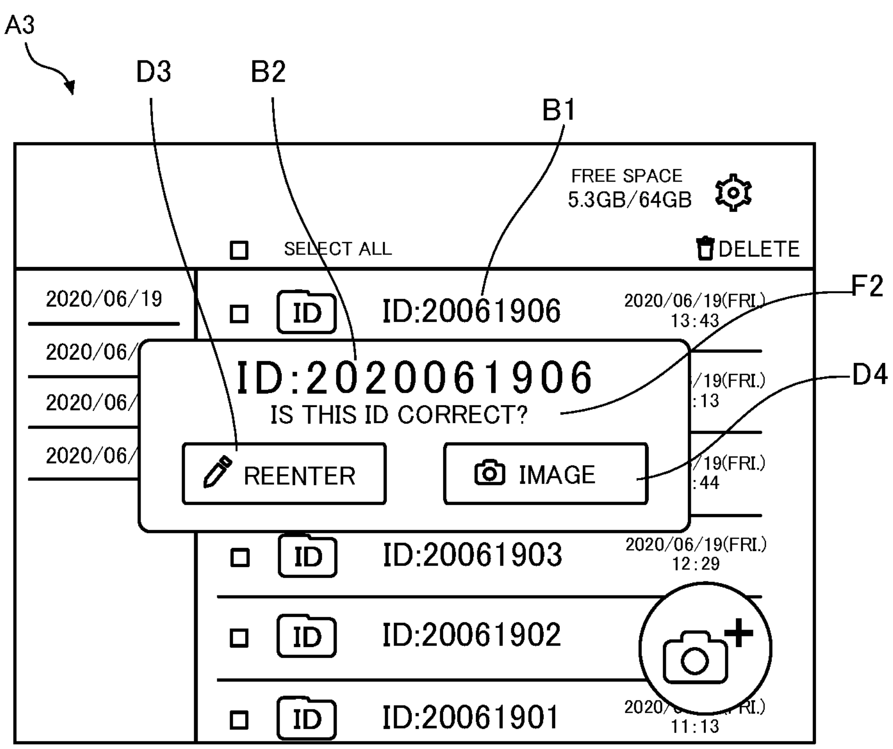

FIGS. 6A and 6B are diagrams illustrating an example of the display screen of the terminal device 120 when an input operation on the imaging start button D1 is accepted on the display screen A1. FIGS. 6A and 6B respectively illustrate a display screen A2 and a display screen A3 which are video display preparation screens of the medical application. A message F1 prompting the input of the identification information, an input form E of the identification information, and an input complete button D2 of the identification information are displayed in an overlaid manner on the display screen A2. Note that the identification information is input to the input form E using the software key displayed on the display screen A1.

The input identification information B2, a confirmation message F2 for the input identification information, a button D3 for re-entering the identification information, and a button D4 for starting imaging on the basis of the confirmation that the input identification information is fine are displayed in an overlaid manner on the display screen A3. The input identification information B2 here is information input in the input form E. Note that the input identification information B2 is the same as that for already managing the video data as the management subject identification information B1. Here, in a case where the button D4 is touched, live playback of the video indicated by the real-time video data is started. Note that, although the input of the identification information is required for identifying the subject whose eye to be inspected is imaged in FIGS. 6A and 6B, the input of the identification information as illustrated FIGS. 6A and 6B is not necessary when the necessity of management by the identification information is relatively low, for example, when the object for examination is an animal.

Figure 7A:
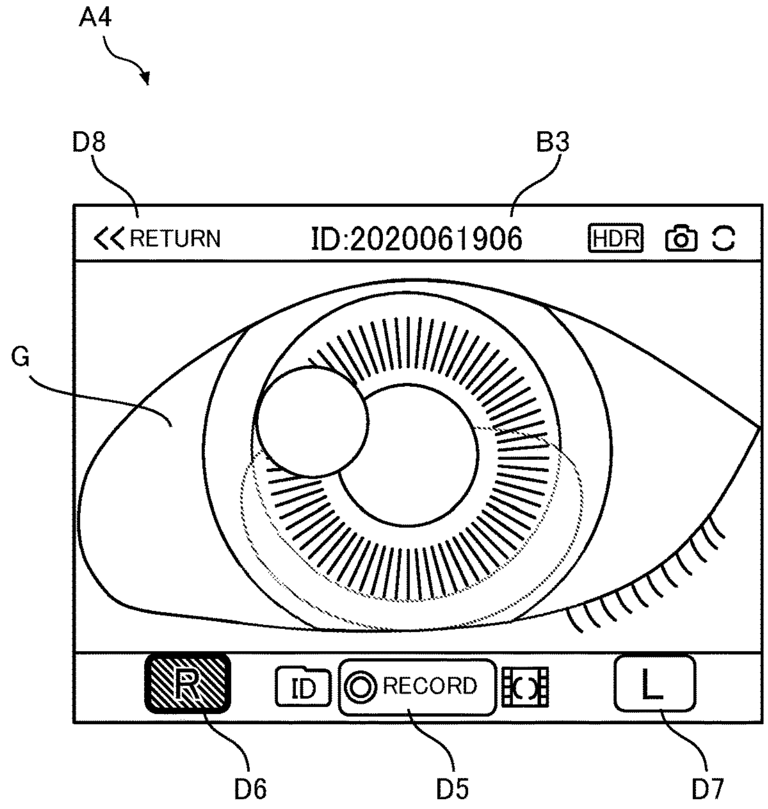
FIGS. 7A and 7B are explanatory diagrams illustrating an example of the display screen of the terminal device 120 corresponding to at least one embodiment of the present invention.
Figure 7B:
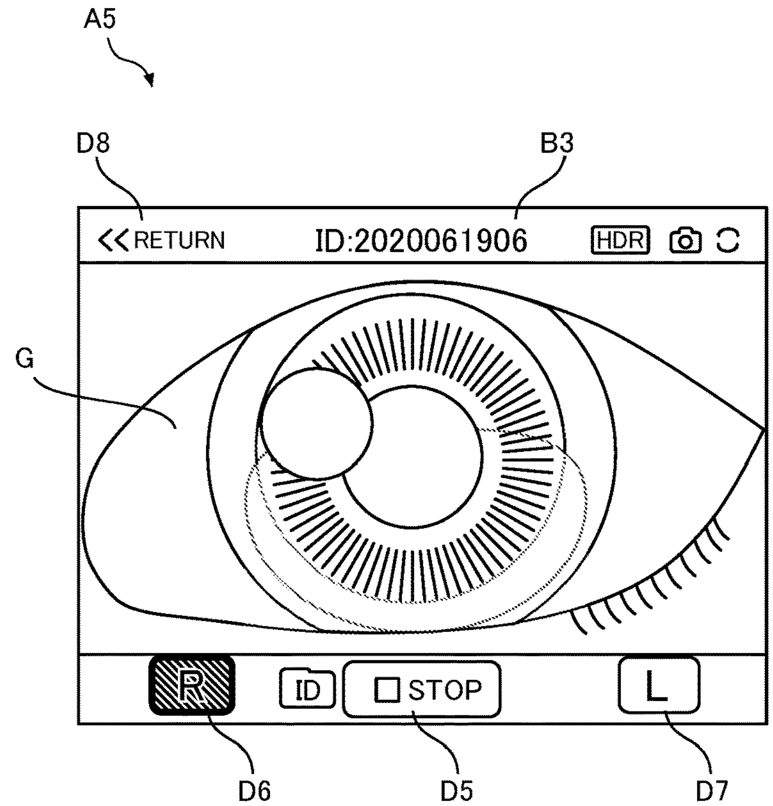

FIGS. 7A and 7B are diagrams illustrating an example of the display screen of the terminal device 120 when an input operation on the button D4 for starting imaging is accepted on the display screen A3. FIGS. 7A and 7B respectively illustrate a display screen A4 and a display screen A5 which are live playback screens of the medical application. Each of the display screen A4 and the display screen A5 displays the subject identification information B3, a video G indicated by the real-time video data, a recording control button D5, a right eye selection button D6, a left eye selection button D7, and a return button D8.

The recording control button D5 is an example of the first button, and is a toggle button for controlling start/stop of recording of the real-time video data which is currently played live. When the recording control button D5 is touched on the display screen A4, recording into the terminal-side recording means is started, and the screen transitions to the display screen A5. On the other hand, when the recording control button D5 is touched on the display screen A5, recording into the terminal-side recording means is stopped, and the screen transitions to the display screen A4. The display mode of the recording control button D5 changes according to the control of start/stop of recording of the real-time video data.

Each of the right eye selection button D6 and the left eye selection button D7 is an example of the third button, and is for selecting either the left eye or the right eye of the subject as the object for examination. When the right eye selection button D6 marked with "R" is touched, the right eye is selected, and when the left eye selection button D7 marked with "L" is touched, the left eye is selected. When either the right eye selection button D6 or the left eye selection button D7 is selected, the right eye selection button D6 and the left eye selection button D7 are displayed in different modes, so that the user can recognize which is selected.

In the examples in FIGS. 7A and 7B, the right eye selection button D6 is operated, and the right eye is selected. When the button corresponding to the selected eye out of the right eye selection button D6 and the left eye selection button D7 is further selected, the selection state is canceled, and both the left and right eyes are not selected. In a case where, when one of the eyes is selected, the button corresponding to the other eye is selected, the selection state of the selected eye is canceled and the other eye is changed to a selected state. When the right eye selection button D6 or the left eye selection button D7 is selected, the video G is recorded in the terminal-side recording means in association with the information regarding the selection of the right eye or the left eye of the subject from the start to the stop of the recording of the real-time video data.

The return button D8 is a button for ending live playback of the video G indicated by the real-time video data and moving the screen to the display screen A1 which is the start screen.

Figure 8:
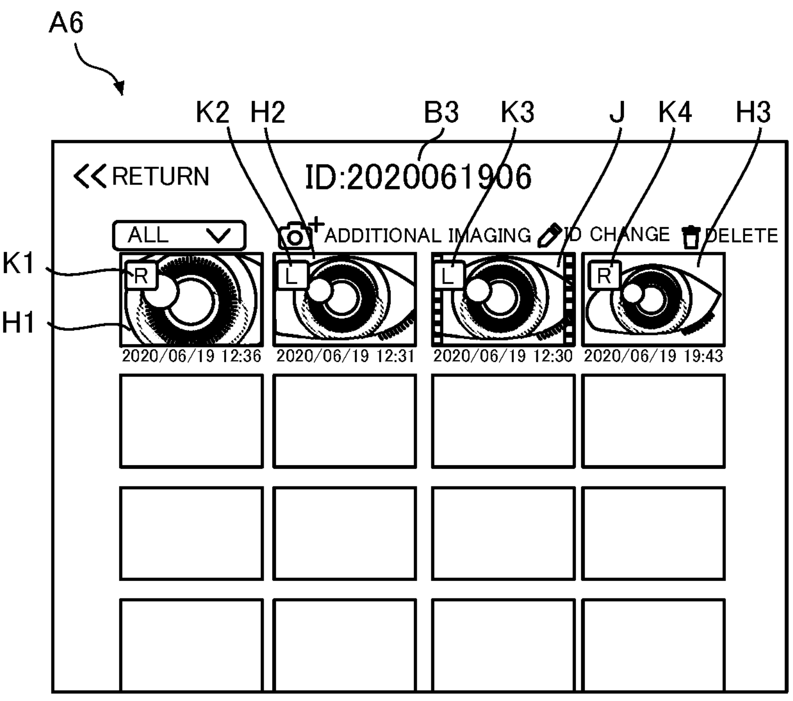
FIG. 8 is an explanatory diagram illustrating an example of the display screen of the terminal device 120 corresponding to at least one embodiment of the present invention.

FIG. 8 is a diagram illustrating an example of the display screen of the terminal device 120 when an operation of selecting any one of the management subject identification information B1 is accepted on the display screen A1. FIG. 8 illustrates a display screen A6 which is a recorded-data list screen of the medical application. The display screen A6 displays the subject identification information B3, a video thumbnail J, still image thumbnails H1 to H3, and left/right selection information K1 to K4.

The video thumbnail J is an image indicating the content of the video indicated by the recorded video data. In the present embodiment, the video thumbnail J is displayed for each recorded video data, and each video thumbnail J is a still image at any moment in the video corresponding to the video thumbnail J. The still image thumbnails H1 to H3 are still images corresponding to still image data (recorded still image data) recorded in the terminal-side recording means.

Here, the recorded still image data refers to data of a still image extracted from a video indicated by the recorded video data and recorded in the terminal-side recording means. An example of the display screen for extracting a still image from a video will be described later. When a touch operation is performed on the video thumbnail J or any one of the still image thumbnails H1 to H3, a video is played or a still image is displayed.

The left/right selection information K1 to K4 are information regarding the selection of the left eye or the right eye of the subject associated with each of recorded video data or recorded still image data. The left/right selection information K1 to K4 indicate that, for the video thumbnail J and the still image thumbnails H1 to H3, the eye indicated in the video data or the still image data is the left eye or the right eye of the subject, respectively. "R" or "L" indicated by the left/right selection information K1 to K4 is determined by a touch operation on the right eye selection button D6 or the left eye selection button D7 illustrated in FIGS. 7A and 7B.

Note that at least one recorded video data or recorded still image data may be transferred to the server device 130 on the basis of a predetermined operation on the display screen A6. For example, in a case where any one of the video thumbnail J and the still image thumbnails H1 to H3 is touched on the display screen A6, a button for selecting one of the playback of the video and display of the still image or data transfer is displayed in an overlaid manner, and the selected operation is executed. Here, regarding the transfer of data, a plurality of recorded video data and/or recorded still image data may be collectively transmitted to the server device 130.

Figure 9:
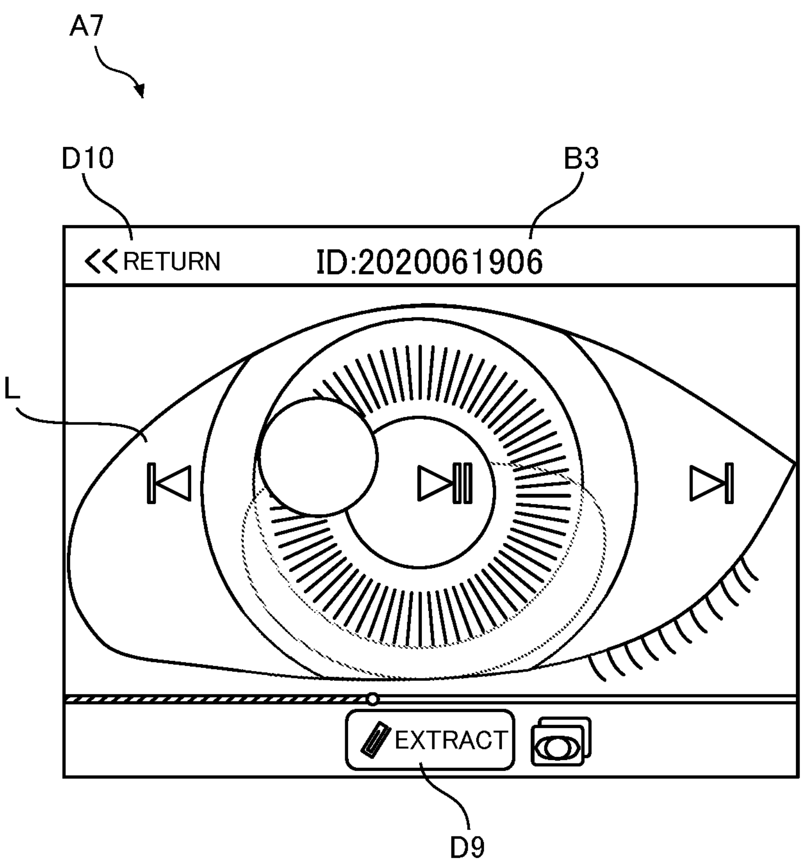
FIG. 9 is an explanatory diagram illustrating an example of the display screen of the terminal device 120 corresponding to at least one embodiment of the present invention.

FIG. 9 is a diagram illustrating an example of the display screen of the terminal device 120 when a selecting operation of selecting the video thumbnail J is accepted on the display screen A6. FIG. 9 illustrates a display screen A7 which is a video playback screen of the medical application. The display screen A7 displays a video L indicated by the recorded video data, the subject identification information B3, a crop button D9, and a return button D10. The video L indicated by the recorded video data corresponds to the video thumbnail J which has been touched on the display screen A6. The return button D10 is a button for ending the playback of the video L and moving the screen to the display screen A6 which is the recorded-data list screen.

The crop button D9 is an example of the second button, and is a button for issuing an extraction request for extracting a still image from a video. Then, when the crop button D9 is touched, the still image data corresponding to the still image displayed on the display screen A7 in the video L is recorded in the terminal-side recording means.

Note that, on the display screen A7, a frame to be displayed among a plurality of frames of the video L can be adjusted by a predetermined operation. For example, when the left part or the right part (or an icon displayed on the left side or the right side) of the display region of the video L is touched on the display screen A7, frame-by-frame rewind or frame-by-frame advance is executed. Furthermore, when the central part (or an icon displayed in the central part) of the display region of the video L is touched on the display screen A7, the playback of the video L is paused or resumed.

Furthermore, the playback range of the video L can also be changed by a predetermined operation on the display screen A7. For example, when a pinch-out operation or a pinch-in operation is performed on the display region of the video L on the display screen A7, the displayed video L is enlarged or reduced. Reducing and displaying the video L means a reduction in enlarging and displaying the video L. When a slide operation is performed on the display region of the video L in a case where the video L is enlarged and displayed, a portion to be enlarged and displayed in the image displayed in the display region of the video L changes.

Note that, when the crop button D9 is touched while the video L is enlarged and displayed, the still image data corresponding to the still image of the enlarged portion in the video L is recorded in the terminal-side recording means. That is, the still image data corresponding to the still image displayed when the crop button D9 is touched is recorded in the terminal-side recording means, regardless of whether or not the video L is enlarged and displayed.

As described above, the medical program for implementing various types of processing in the terminal device 120 used together with the medical examination device 110 including the imaging camera according to the present invention implements: receiving various types of data including video data (real-time video data) that is captured and simultaneously transmitted in real time by the medical examination device 110; playing a video live and displaying the video on the terminal display unit included in the terminal device 120, the video being indicated by the received real-time video data; controlling start/stop of recording of the real-time video data which is currently played live on the basis of a predetermined operation on the terminal device 120; and recording the real-time video data into the terminal-side recording means as recorded video data during a period from the start to the stop of recording. Thus, the medical program enables the video data generated by imaging by the medical examination device 110 to be played live and recorded while maintaining usability of the medical examination device 110.

That is, the video can be played live and recorded by an operation on a display screen of an application executed by the terminal device 120, by which the video can be played live and recorded without applying, to the medical examination device 110, a change in configuration that would impair the usability of the medical examination device 110.

Second Embodiment

Conventionally, still image data is extracted from video data and recorded. The reason for recording the still image data is that a still image of a specific frame of the video data is desired to be used for a specific purpose. For example, there is an apparatus that temporarily stores a video generated by imaging an eye to be inspected of a patient by a medical imaging device, displays the video, and records still image data of a frame selected by a user for use in an examination or the like in a recording means included in the apparatus.

Here, the above apparatus requires the user to select desired still image data in order to record the still image data in the recording means, and thus, has a problem of imposing a large work burden on the user. On the other hand, if the video data is directly stored in a storage such as a hard disk drive (HDD) or a solid state drive (SSD) without being recorded in units of frames, the still image data can be extracted later over time. However, since the volume of the video data is very large as compared with the still image data, the remaining space where data can be recorded of the recording means provided in the apparatus is reduced. Thus, the apparatus has a problem of imposing a burden on the user such as management of video data in consideration of the remaining capacity.

An example of an image processing device 220 according to an embodiment of the present invention will be described below with reference to the drawings.

Figure 10:
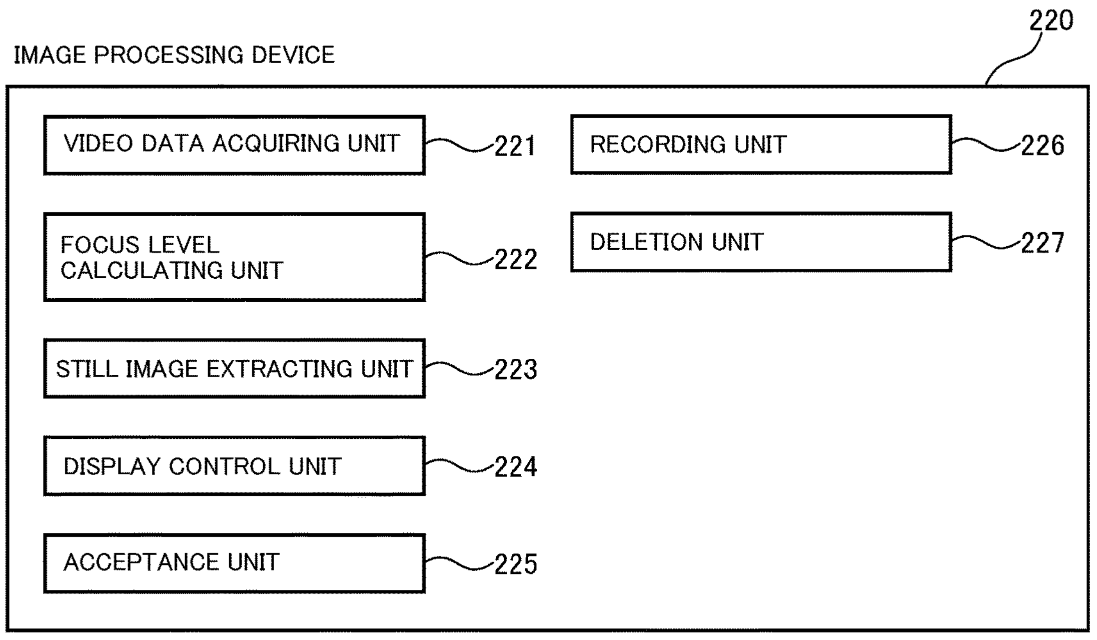
FIG. 10 is a block diagram illustrating an example of the functional configuration of an image processing device 220 corresponding to at least one embodiment of the present invention.

FIG. 10 is a block diagram illustrating an example of the functional configuration of an image processing device 220 corresponding to at least one embodiment of the present invention.

The image processing device 220 is an example of a computer according to the present invention. The image processing device 220 acquires video data to be processed, and calculates focus levels of some or all frames constituting the acquired video data. Then, the image processing device 220 extracts, as extraction still image data, some or all of the frames (candidate frames) having focus levels equal to or greater than a predetermined value among the frames whose focus levels have been calculated, and records the extraction still image data in a recording means included in the image processing device. Here, the focus level means a degree of focusing on an object in the frame. A feature of the present invention is to automatically extract extraction still image data on the premise that image data having a high focus level is highly likely to be an image desired by a user.

As illustrated in FIG. 10, the image processing device 220 includes a video data acquiring unit 221, a focus level calculating unit 222, a still image extracting unit 223, a display control unit 224, an acceptance unit 225, a recording unit 226, and a deletion unit 227.

The video data acquiring unit 221 has a function of acquiring video data to be processed. The video data to be processed is not particularly limited, but is preferably captured video data. The video data in the present embodiment is video data transmitted from an external device, and the video data acquiring unit 221 receives and acquires the video data. As will be described later, video data captured by an ophthalmic imaging device is assumed as one of video data to be processed, but the image processing device 220 according to the present embodiment is not applied only to the ophthalmic field, and can be applied to video data in a wide range of fields.

In addition, the video data acquiring unit 221 stores the acquired video data in a storage means included in the computer. The storage means here is a means that temporarily holds video data. For example, the storage means is implemented by a memory. Furthermore, the storage means may be implemented by handling the video data as a temporary file. The video data stored in the storage means is deleted with, for example, termination of an application related to extraction of extraction still image data as a trigger. In a case where the video data is treated as a temporary file, the video data may be held in a storage such as an HDD or an SSD.

The focus level calculating unit 222 has a function of calculating focus levels of some or all frames constituting the video data.

Here, the focus level is calculated for each frame that is an object for calculation. The configuration for specifying the frame whose focus level is to be calculated among the frames constituting the video data is not particularly limited. In addition, the focus level is preferably calculated on the basis of an amount of edge extracted from the still image data. The calculated focus level is used as a focus score by the still image extracting unit 223 described later.

In addition, the calculation of the focus level by the focus level calculating unit 222 may be achieved by edge extraction image generating processing of executing edge extraction processing on a frame constituting the video data to generate an edge extraction image, and calculation processing of calculating the focus level of the frame corresponding to the edge extraction image on the basis of edge distribution in the edge extraction image.

Here, the edge extraction processing means processing of extracting, as an edge, a portion where a change in the luminance value in the image is sharp (a portion where the luminance value is discontinuously changed). The edge extraction processing may be executed using a Laplacian filter. The Laplacian filter here is, for example, an 8-neighbor Laplacian filter with a size of 3×3. Note that the edge extraction processing may be executed using any of various known techniques as long as an edge can be extracted. In addition, the calculation processing is not particularly limited as long as it is based on an amount of edges in the edge extraction image, but conceivable examples include processing of setting the edge distribution in the edge extraction image as the focus level of the frame corresponding to the edge extraction image.

Furthermore, the focus level calculating unit 222 may execute green component image generating processing of extracting a green component from color information of each pixel constituting the frame to generate green component image data and grayscale processing of converting the green component image data into grayscale to generate grayscale image data, and calculate the focus level on the basis of the grayscale image data obtained by the grayscale processing.

Here, the green component means a green component in three primary colors used in RGB (red, green, blue) which is one of image expression formats. The green component image is an image obtained by removing a red component and a blue component of three primary colors used in RGB from a still image of the frame. Converting into grayscale means that the colors used in the image are converted into only white, black, and at least one level of gray. In general, only luminance information is extracted from a color image, and a gradual change from black to white is expressed according to a gradation range of luminance.

For example, when the video data is data of a video obtained by imaging an object with blue background illumination, and a green component image is generated by extracting a green component and is converted into grayscale, the obtained image has a higher contrast as compared with an image that is not converted into grayscale. Therefore, a frame having a high focus level can be more accurately extracted. In addition, the calculation result of the focus level is not greatly affected even if a green component image is generated in video data in which the background illumination is not blue. Therefore, if the configuration for generating the green component image is applied, it is possible to calculate the focus level with sufficient accuracy regardless of the color of the background illumination.

In particular, in tests in the field of ophthalmology, blue background illumination and fluorescein staining are used in combination. In an image obtained by capturing the eye of a subject using this combination, the blue component and the green component are more than the red component. When the edge extraction processing is directly performed on the frame constituting the video data captured in this manner, the edge is not successfully extracted, and as a result, a sufficient focus level may not be calculated. Here, a portion to be actually observed in the combination of the blue background illumination and the fluorescein staining is a green component portion. Therefore, by applying the configuration of generating a green component image and converting the green component image into grayscale during the calculation of the focus level, the focus level of a frame in which a portion to be observed is in focus can be calculated to be larger. Here, the blue component is removed from the video data captured by applying a barrier filter to the combination of the blue background illumination and the fluorescein staining. Therefore, even if the green component image obtained by extracting the green component is used, there is no problem in calculating the focus level. In addition, the calculation result of the focus level is not greatly affected even if a green component image is generated and the edge extraction processing is performed on video data of the eye of the subject imaged with background illumination of another color. For this reason, it is possible to uniformly apply the configuration of generating the green component image.

Furthermore, the focus level calculating unit 222 may execute adjustment processing of adjusting the black level of the grayscale image data, and calculate the focus level on the basis of the grayscale image data which has been adjusted in black level by the adjustment processing.

Here, the degree of adjustment of the black level is appropriately determined according to the type of an object to be imaged as the video. By adjusting the black level, noise of the grayscale image is reduced, whereby the influence of the noise in the calculation of the focus level can be reduced. As a result, the focus level can be more accurately calculated.

Furthermore, the focus level calculating unit 222 may set one frame among the frames constituting the video data as the target frame whose focus level is to be calculated at predetermined time intervals or every predetermined number of frames. The predetermined time intervals and the predetermined number of frames are appropriately determined according to, for example, performance of the image processing device 220, specifications of software, and the like. With such a configuration, the processing time by the image processing device 220 can be shortened.

In addition, when the video data is data of a video obtained by imaging the eye of the subject, the focus level calculating unit 222 may calculate the focus level for a region excluding a region of a predetermined range on the upper side and/or the lower side of the frame constituting the video data.

For example, when the focus level of the video data obtained by imaging the eye of the subject is calculated, the calculation result of the focus level is affected by the region of a predetermined range on the upper side and/or the lower side of the frame, although the region is not used for examination. The region on the upper side of the frame that is not used for examination is, for example, the eyelash region of the subject. On the other hand, when the region including a portion not used for examination is excluded from the target for calculation of the focus level, the focus level of the frame focused on the region that can be used for examination is calculated to be larger. Furthermore, the processing time by the image processing device 220 is reduced by limiting the region to be set as a target for calculation of the focus level. The region of the predetermined range on the upper side and/or the lower side of the frame is appropriately determined, and is, for example, ¼ of each of the upper side and the lower side of the frame.

The still image extracting unit 223 has a function of extracting, as extraction still image data, some or all of the frames (candidate frames) having focus levels equal to or greater than a predetermined value among the frames whose focus levels have been calculated. Here, the predetermined value is a predetermined focus level threshold. The threshold is appropriately set, for example, in consideration of the content of an object to be imaged in the video data and the upper limit number related to extraction.

In addition, in a case where there are multiple candidate frames within a preset time range when the candidate frames are arranged in chronological order, the still image extracting unit 223 may exclude a predetermined number of candidate frames from frames to be extracted in descending order of the focus level.

The preset time range is appropriately determined. Excluding the predetermined number of candidate frames from the frames to be extracted means that the predetermined number of candidate frames are not treated as the extraction still image data. Due to the exclusion from the frames to be extracted within a preset time range, the number of candidate frames extracted within a specific time range can be reduced, and thus, the total volume of the extraction still image data to be recorded in the recording means can be reduced. Suppose there are five candidate frames within a preset time range, for example. In this situation, when two candidate frames are set to be excluded from the frames to be extracted in descending order of the focus level, two candidate frames with a small focus level are excluded and three candidate frames remain within the time range.

When the still image extracting unit 223 sequentially focuses on the candidate frames in chronological order during extraction of extraction still image data from the candidate frames, and there is a candidate frame having a focus level smaller than that of a frame of interest within a predetermined time range from the time point of the frame of interest, the still image extracting unit 223 may exclude the candidate frame from the frames to be extracted.

Here, sequentially focusing on the candidate frames in chronological order means that the candidate frames are specified as the frame of interest in chronological order. The chronological order here may be from the previous frames to the latest frames or from the latest frames to the previous frames. In addition, the configuration for specifying the time point within the predetermined time range from the frame of interest is not particularly limited, and a configuration for specifying a time point before or after the time point of the frame of interest by a predetermined time range may be adopted.

For example, when the video data to be processed is data of a video obtained by continuously imaging a plurality of objects (for example, the right eye and the left eye of the subject), and an average value of the magnitudes of the focus levels of the frames is calculated for each imaged object, the average values may be different between the imaged objects. That is, the video data may include a portion of the imaged object where frames having large focus levels are collected and a portion of the imaged object where frames having focus levels slightly lower than those of the abovementioned frames are collected. Specifically, there may be a situation in which the distribution of magnitudes of focus levels is not uniform because of the switching of the imaged objects. In such a situation, if the extraction processing is executed by selecting candidate frames in descending order of the focus level until the number of frames reaches a predetermined upper limit number, a sufficient number of frames may not be extracted depending on imaged objects, and thus, a situation occurs in which extraction still image data for each imaged object cannot be sufficiently obtained. On the other hand, when there are multiple candidate frames within a predetermined time range from the time point of the frame of interest, and some of the multiple candidate frames within the predetermined time range are excluded from the frames to be extracted, a situation in which the extraction of the extraction still image data is performed only from some of the imaged objects can be avoided. As a result, the possibility that the candidate frame corresponding to another imaged object remains as the frames to be extracted is increased. That is, it can be said that there is a high possibility that the extraction still image data is uniformly obtained for each of the imaged objects.

Further, when extracting the extraction still image data from the candidate frame, the still image extracting unit 223 may exclude a frame having the minimum focus level among the candidate frames from the frames to be extracted so that the total number of the extraction still image data does not exceed a predetermined upper limit number. Here, the total number of the extraction still image data is not particularly limited, but is preferably determined on the basis of the recording capacity or the like of the recording means of the image processing device 220. In addition, the configuration for preventing the total number from exceeding the predetermined upper limit number is not particularly limited. For example, when the total number is going to exceed the upper limit number, the total number may be decreased to avoid this situation, and when the total number reaches a predetermined threshold smaller than the upper limit number, the total number may be decreased. With such a configuration, it is possible to reduce the user's burden of managing the recording capacity for the extraction still image data.

The display control unit 224 has a function of displaying the extraction still image indicated by the extraction still image data on a display unit included in the image processing device 220. An example of the display unit is a touch panel display.

Furthermore, in a case where a predetermined first input operation is performed, the display control unit 224 may display the video indicated by the video data including the extraction still image on the display unit. Examples of the first input operation include an operation of selecting an extraction still image indicated by the extraction still image data displayed on the display unit, a thumbnail image of the extraction still image, and a predetermined video replay button.

In addition, in a case where a predetermined second input operation is performed on any of the extraction still images indicated by the extraction still image data, the display control unit 224 may continue to play the video data from the extraction still image data. Examples of the second input operation include an operation of selecting an extraction still image indicated by the extraction still image data or a thumbnail image of the extraction still image, and an operation of selecting a predetermined video replay button when the extraction still image is displayed on the display unit. With this configuration, the user can confirm whether or not there is a frame to be recorded before and after the time point of the frame corresponding to the extraction still image data.

The acceptance unit 225 has a function of accepting a selecting operation of selecting the extraction still image displayed on the display unit from the user. Furthermore, the acceptance unit 225 may accept a selecting operation of selecting a frame of the video being displayed. Examples of the selecting operation of selecting the extraction still image or a frame of the video being displayed include an operation of selecting a button corresponding to the extraction still image or a frame of the video being displayed.

The recording unit 226 has a function of recording the extraction still image data in a recording means included in the image processing device 220. Here, unlike the storage means described above, the recording means constantly holds data. For example, the recording means is implemented by a storage such as an HDD or an SSD.

In addition, when the selecting operation of selecting the extraction still image displayed on the display unit is accepted, the recording unit 226 may record, in the recording means, extraction still image data indicating the extraction still image selected by the selecting operation that has been accepted. By recording the extraction still image data indicating the extraction still image selected by the user, it is possible to suppress an increase in the total volume of the extraction still image data to be recorded.

In addition, when the selecting operation of selecting the frame of the video displayed on the display unit is accepted, the recording unit 226 may record, in the recording means, still image data indicating the frame selected by the selecting operation that has been accepted. As described above, even when there is nothing to be recorded in the extraction still image, it is possible to play a video on the basis of an operation from the user and record still image data of a frame desired by the user in the recording means.

The deletion unit 227 has a function of deleting video data stored in the storage means at a predetermined timing (first timing) after the still image extracting unit 223 extracts extraction still image data.

Here, the first timing is not particularly limited as long as it is after the extraction of the extraction still image data, and may be a timing at which the still image extracting unit 223 extracts the extraction still image data, or may be a timing at which the recording unit 226 records the extraction still image data in the recording means. In addition, the first timing may be a timing at which a predetermined time has elapsed after the extraction of the extraction still image data, or may be a timing at which an application related to the extraction of the extraction still image data ends.

The example of the functional configuration of the image processing device 220 corresponding to at least one of the embodiments of the present invention has been described above. Note that, in the example described with reference to FIG. 10, the video data acquired by the video data acquiring unit 221 is deleted from the storage means by the deletion unit 227 at the first timing after the extraction still image data is extracted, but the timing of deleting the video data is not limited thereto. The deletion unit 227 may delete the video data stored in the storage means at a predetermined timing (second timing) after the video data is stored in the storage means, even when the still image extracting unit 223 does not extract the extraction still image data. The condition of the second timing is not particularly limited as long as the second timing is after the video data is stored in the storage means, but for example, it is conceivable that the trigger of the second timing is that the user who intends to leave the video data stored in a temporary storage means executes processing of copying the video data to a permanently recordable recording means. In a case where it can be confirmed that the video data has been duplicated in a storage such as an HDD or an SSD that can permanently record data, the necessity of leaving the video data in the temporary storage means is lost, and thus the video data is deleted from the temporary storage means.

Figure 11:
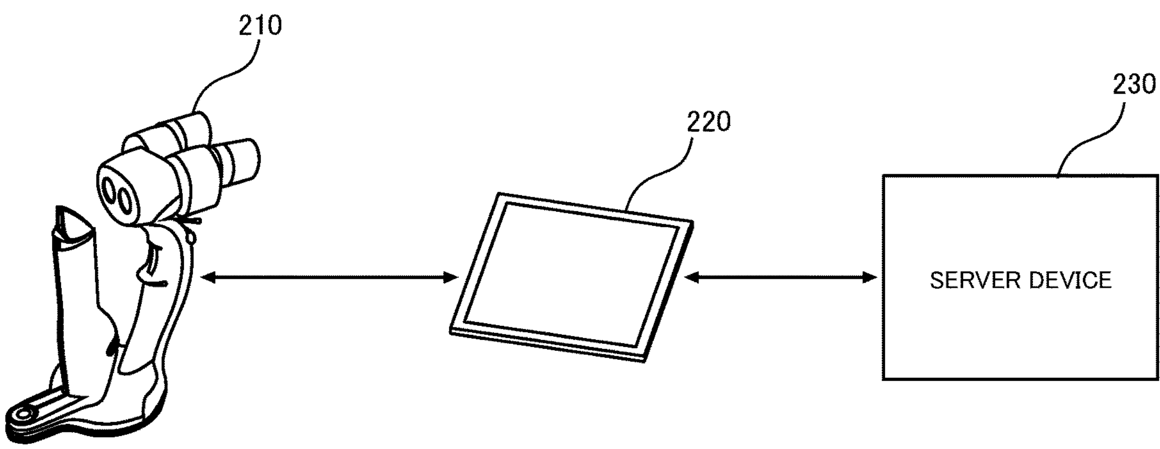
FIG. 11 is an explanatory diagram for describing an example of an environment where the image processing device 220 corresponding to at least one embodiment of the present invention is applied.

FIG. 11 is an explanatory diagram for describing an example of an environment where the image processing device 220 corresponding to at least one embodiment of the present invention is applied. FIG. 11 illustrates a medical examination device 210, the image processing device 220, and a server device 230.

The medical examination device 210 is a device for examining an object for examination. The object for examination is, for example, a human or an animal. The medical examination device 210 includes at least an imaging camera and has a function of imaging the object for examination and generating video data. The medical examination device 210 also has a communication function, and performs wireless communication with the image processing device 220 in the present embodiment. The medical examination device 210 transmits the video data generated by imaging to the image processing device 220. Note that, in a case where the medical examination device 210 performs wired communication with the image processing device 220, the medical examination device 210 and the image processing device 220 are connected by, for example, a USB cable or the like. Note that, in the example illustrated in FIG. 11, the medical examination device 210 captures a video, but the device that captures a video is not limited to the medical examination device 210, and any device can be used as long as it can capture a video.

In the present embodiment, the medical examination device 210 is a handheld device called a slit lamp that irradiates the eye of the subject with slit light and observes scattered light generated by scattering in the subject's eye, thereby inspecting a cornea, a crystalline lens, or the like of the subject's eye. Note that the medical examination device 210 is not limited to have the above configuration, and can be any of various medical devices including a handheld medical examination device such as a handheld fundus camera and a stationary medical device such as a testing device for dry eyes, in addition to the handheld slit lamp.

The image processing device (terminal device) 220 in FIG. 11 is used together with the medical examination device 210. In FIG. 11, the terminal device functions as the image processing device 220.

The image processing device 220 may be a device designed as a dedicated machine, but can be implemented by a general computer. That is, the image processing device 220 includes at least a CPU that would be commonly included in a general computer and a memory. Processing in the image processing device 220 is implemented by reading a program for executing the processing from the memory and executing the program in a CPU or a GPU that functions as a control circuit. In other words, a processor is configured to be able to execute the processing of each device by executing the program. Hereinafter, any device is applicable as the image processing device 220 as long as it can execute processing equivalent to that of a computer, and the image processing device 220 can also be implemented by, for example, a smartphone, a tablet terminal, or the like. In the present embodiment, the image processing device 220 is a tablet terminal.

The image processing device 220 has a function of communicating with the medical examination device 210 and the server device 230. Specifically, the image processing device 220 performs wireless communication with the medical examination device 210 and performs wired or wireless communication with the server device 230 to transmit and receive various types of information.

Furthermore, the image processing device 220 includes a display unit, and displays various types of information on the display unit. Specifically, the image processing device 220 displays the extraction still image and the video indicated by the video data on the display unit. In the present embodiment, the image processing device 220 which is a tablet terminal includes a touch panel functioning as the display unit, displays various types of information including the extraction still image, the video indicated by the video data, and the like on the touch panel, and accepts various input operations from the user by a touch operation on the touch panel.

The server device 230 manages various types of information such as the video data transmitted from the image processing device 220. The server device 230 includes a server-side recording means that records the video data and the still image data received from the image processing device 220. The data recorded in the server-side recording means may be classified and managed on the basis of the identification information. In the present embodiment, the server device 230 records the extraction still image data in the server-side recording means included in the server device 230 in association with an electronic medical record corresponding to the subject on the basis of the identification information associated with the extraction still image. Note that the server-side recording means that records the extraction still image data transmitted from the image processing device 220 is not particularly limited. Another example of the server-side recording means that records the still image data transmitted from the image processing device 220 includes a recording means belonging to the same network as the server device 230.

Communication between the server device 230 and the image processing device 220 may be established by wired connection using, for example, a USB cable, or may be established by wireless communication such as using a wireless LAN. Note that the server device 230 is, for example, a device that manages electronic medical records or the like installed in an in-hospital LAN of a hospital.

Figure 12:
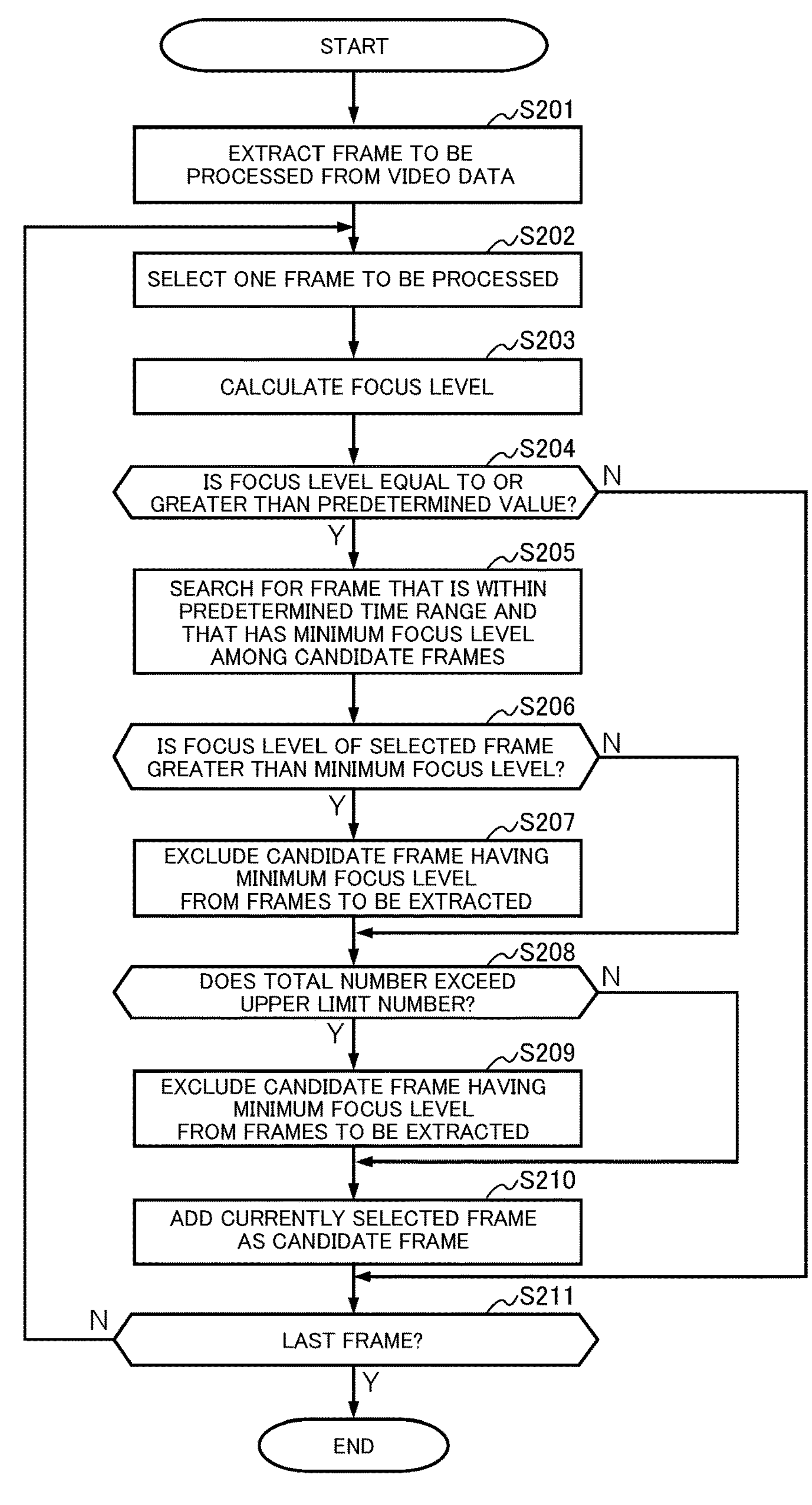
FIG. 12 is a flowchart illustrating an example of a flow of frame extraction processing performed by the image processing device 220 corresponding to at least one embodiment of the present invention.

FIG. 12 is flowchart illustrating an example of a flow of frame extraction processing performed by the image processing device 220 corresponding to at least one embodiment of the present invention.

In FIG. 12, the extraction processing by the image processing device 220 is started by extracting a frame to be processed from the video data (step S201). In the present embodiment, the extraction processing by the image processing device 220 is started by extracting one frame as a frame to be processed from a plurality of frames constituting the video data at predetermined time intervals.

Next, the image processing device 220 selects any one of the frames to be processed extracted in step S201 (step S202). In the present embodiment, the image processing device 220 selects one frame at the earliest time point that has not yet been selected when the frames to be processed are arranged in chronological order.

Next, the image processing device 220 calculates the focus level of the frame selected in step S202 (step S203). In the present embodiment, the image processing device 220 executes the edge extraction processing using the Laplacian filter on the frame selected in step S202 to generate an edge extraction image, and calculates the focus level of the frame corresponding to the edge extraction image on the basis of the edge distribution in the edge extraction image.

Next, when the focus level calculated in step S203 is not equal to or greater than a predetermined value (N in step S204), the image processing device 220 proceeds to step S211.

On the other hand, when the focus level calculated in step S203 is equal to or greater than the predetermined value (Y in step S204), the image processing device 220 searches for a frame having the minimum focus level among the candidate frames within the predetermined time range (step S205). In the present embodiment, the image processing device 220 searches for a frame that is within the predetermined time range and that has the minimum focus level among the candidate frames added to the candidate frame list.

Next, when the focus level of the frame selected in step S202 is smaller than the minimum focus level searched in step S205 (N in step S206), the image processing device 220 proceeds to step S208.

On the other hand, when the focus level of the frame selected in step S202 is larger than the minimum focus level searched in step S205 (Y in step S206), the image processing device 220 excludes the candidate frame having the minimum focus level searched in step S205 from the frames to be extracted (step S207). In the present embodiment, the image processing device 220 deletes the candidate frame having the minimum focus level searched in step S205 from the candidate frame list.

Next, when the total number of candidate frames does not exceed the upper limit number (N in step S208), the image processing device 220 proceeds to step S210.

On the other hand, when the total number of candidate frames exceeds the upper limit number (Y in step S208), the image processing device 220 excludes the frame having the minimum focus level among the candidate frames from the frames to be extracted (step S209). In the present embodiment, the image processing device 220 deletes the candidate frame having the minimum focus level from the candidate frame list.

Next, the image processing device 220 adds the currently selected frame as a candidate frame (step S210). In the present embodiment, the image processing device 220 adds information for specifying the currently selected frame to the candidate frame list.

Next, when the selected frame is not the last selected frame in the frames to be processed (N in step S211), the image processing device 220 returns to step S202.

On the other hand, when the selected frame is the last selected frame in the frames to be processed (Y in step S211), the image processing device 220 ends the frame extraction processing.

An example of the flow of the frame extraction processing performed by the image processing device 220 has been described above. Note that, in the example illustrated in FIG. 12, the image processing device 220 performs a series of processes from the calculation of the focus level for one frame to the determination of excluding or adding the candidate frame, but the present invention is not limited thereto. For example, the image processing device 220 may be configured to collectively perform the calculation processing of calculating the focus level for each of the plurality of frames, and then collectively perform the processing of excluding or adding the candidate frame.

Figure 13:
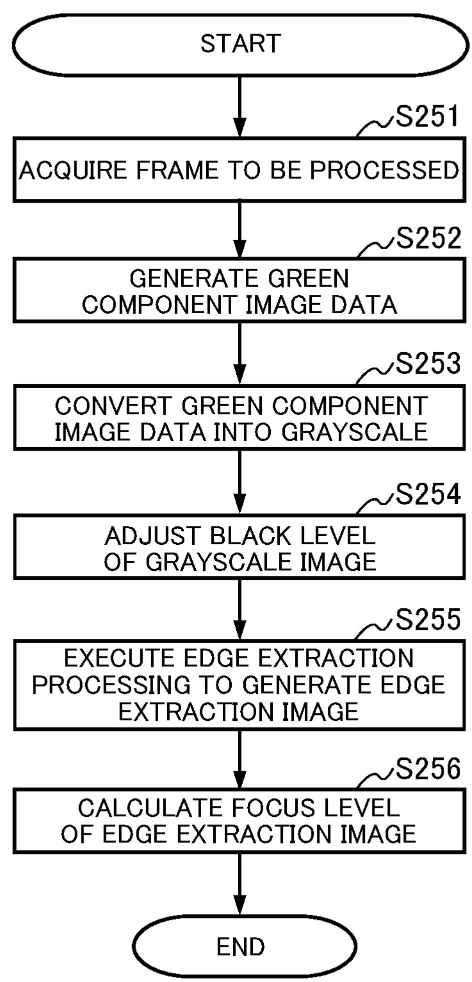
FIG. 13 is a flowchart illustrating an example of a flow of focus level calculation processing of calculating the focus level of a frame by the image processing device 220 corresponding to at least one embodiment of the present invention.

FIG. 13 is flowchart illustrating an example of a flow of focus level calculation processing of calculating the focus level of a frame by the image processing device 220 corresponding to at least one embodiment of the present invention. In FIG. 13, an example of a detailed flow of the focus level calculation processing in step S203 in FIG. 12 will be described.

In FIG. 13, the focus level calculation processing by the image processing device 220 is started by acquiring a frame to be processed from the video data (step S251). In the present embodiment, the focus level calculation processing by the image processing device 220 is started by acquiring the frame selected in step S202 in FIG. 12 from a plurality of frames constituting the video data.

Next, the image processing device 220 generates green component image data obtained by extracting a green component of the color information of each pixel constituting the selected frame (step S252). In the present embodiment, the image processing device 220 generates green component image data of only the green component obtained by removing the red component and the blue component of the frame.

Next, the image processing device 220 converts the green component image data into grayscale to generate grayscale image data (step S253).

Next, the image processing device 220 adjusts the black level of the grayscale image data (step S254). In the present embodiment, the image processing device 220 adjusts the black level of the grayscale image data so that noise on the image is canceled.

Next, the image processing device 220 executes the edge extraction processing on the grayscale image data with the adjusted black level to generate an edge extraction image (step S255). In the present embodiment, the image processing device 220 executes the edge extraction processing using a Laplacian filter on the grayscale image data with the adjusted black level to generate an edge extraction image.

Next, the image processing device 220 calculates the focus level of the edge extraction image (step S256), and ends the focus level calculation processing. In the present embodiment, the image processing device 220 executes processing of calculating the edge distribution in the edge extraction image and setting the edge distribution as the focus level of the frame corresponding to the edge extraction image, and ends the focus level calculation processing. Furthermore, in the present embodiment, the calculated focus level is treated as a focus score.

An example of the flow of the focus level calculation processing of calculating the focus level of the frame by the image processing device 220 has been described above.

Figure 14:
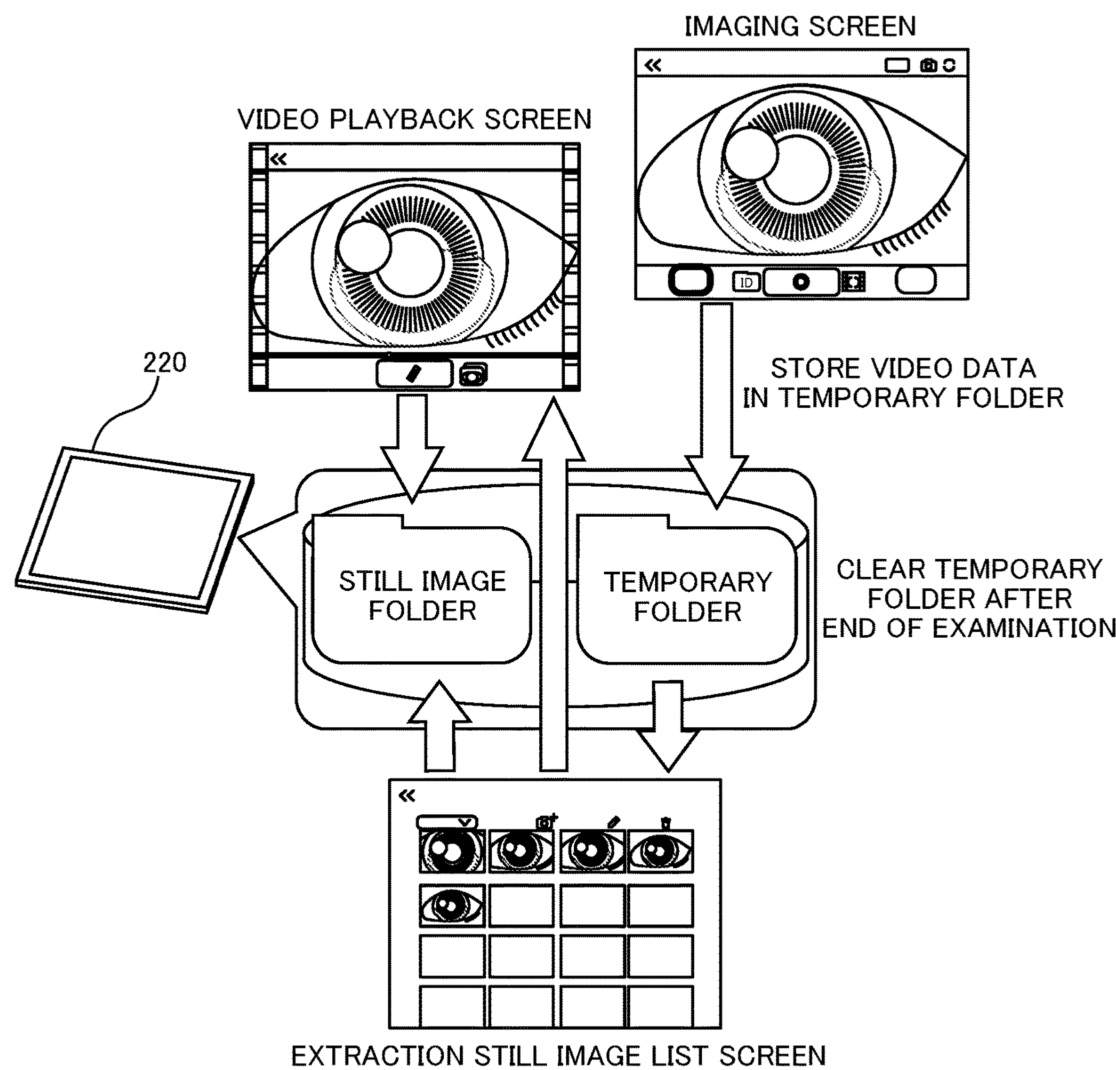
FIG. 14 is an explanatory diagram for describing an example of management of video data and still image data in the image processing device 220 corresponding to at least one embodiment of the present invention.

FIG. 14 is an explanatory diagram for describing an example of management of video data and still image data in the image processing device 220 corresponding to at least one embodiment of the present invention.

In the example illustrated in FIG. 14, the image processing device 220 manages video data by a temporary folder, and manages extraction still image data by a still image folder. FIG. 14 illustrates a flow of imaging the eye of the subject and selecting and storing a frame in focus during the examination of the eye of the subject. Here, the work from the imaging of the eye of the subject to the recording of the focused frame in the recording means of the image processing device 220 is referred to as "examination".

First, an imaging screen illustrated in FIG. 14 indicates a state of imaging by the medical examination device 210 in the examination of the subject, the imaging screen being received in real time by the image processing device 220 and being displayed on the display unit. The image processing device 220 stores the received video data in the temporary folder as a temporary file. Then, the image processing device 220 calculates the focus levels of the frames constituting the video data stored in the temporary folder, and handles the frames having focus levels equal to or greater than a predetermined value as the extraction still image data.

An extraction still image list screen illustrated in FIG. 14 is a screen that displays a list of extraction still images of the extraction still image data after the eye of the subject is imaged. Here, the user selects and touches the extraction still image to be stored on the extraction still image list screen. The image processing device 220 records the extraction still image data indicating the extraction still image selected by the user in the still image folder. The image processing device 220 deletes the video data from the temporary folder with the recording of the extraction still image data in the still image folder as a trigger.

A video playback screen illustrated in FIG. 14 is a screen for playing video data in response to a predetermined operation on the extraction still image list screen. For example, in a case where an operation of playing a video is performed on the extraction still image displayed on the extraction still image list screen, the image processing device 220 continues to play the video from the extraction still image. Then, when an operation of designating a predetermined frame is performed on the video playback screen, still image data of the designated frame may be recorded in the still image folder.

By managing video data and still image data in this manner, it is possible to reduce the volume of data stored in the image processing device 220 while leaving still image data desired by the user.

The example of managing the video data and the still image data in the image processing device 220 has been described above. Note that, in the example described with reference to FIG. 14, the video data is deleted with the recording of the extraction still image data in the still image folder as a trigger after being stored in the temporary folder, but the method of managing the video data is not limited thereto. For example, when an operation of instructing recording of the video data stored in the temporary folder by the user is accepted, the image processing device 220 may record the video data in a video recording folder (not illustrated) that constantly stores the video data. With such a configuration, it is possible to give the user an option of leaving the video data without deleting the video data even after the end of the examination, whereby the user can more flexibly manage the video data and the still image data.

Figure 15:
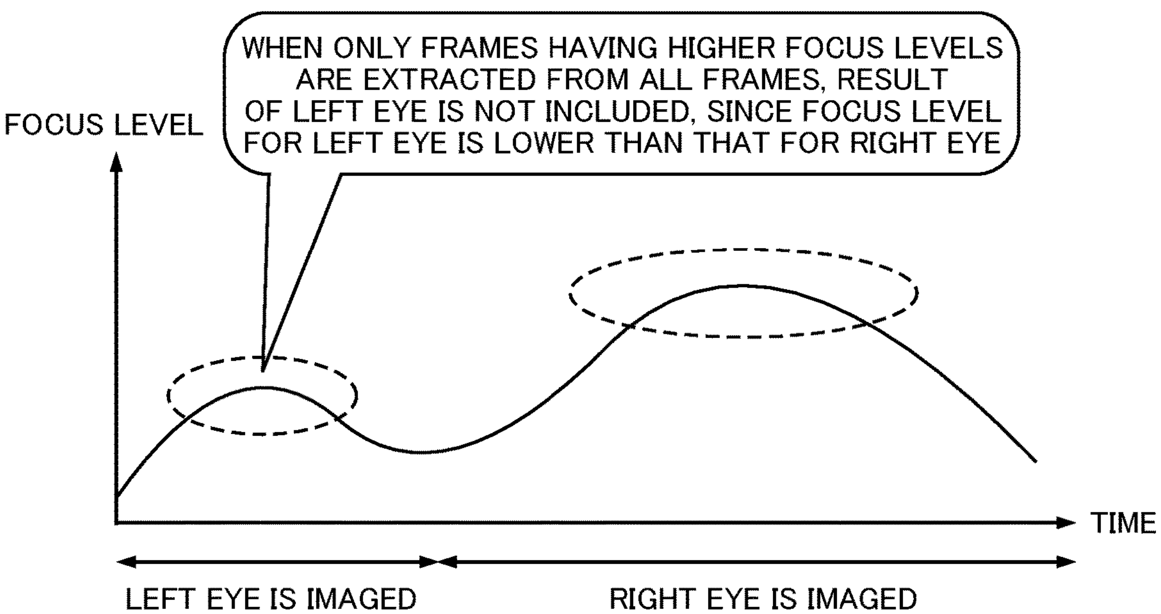
FIG. 15 is an explanatory diagram for describing an example of processing, performed by the image processing device 220 corresponding to at least one embodiment of the present invention, of extracting extraction still image data from a candidate frame.

FIG. 15 is an explanatory diagram for describing an example of processing, performed by the image processing device 220 corresponding to at least one of the embodiments of the present invention, of extracting the extraction still image data from a candidate frame. FIG. 15 illustrates a graph of a change in focus level when candidate frames in the video data are arranged in chronological order.

In the example illustrated in FIG. 15, first, the left eye of the subject is imaged, and then the right eye of the subject is imaged. In the graph illustrated in FIG. 15, one portion where the focus level is great is present on the side where the left eye is imaged, another one is present on the side where the right eye is imaged, and a portion where the focus level is small is present between these portions. This is because the focus level temporarily decreases when the object to be imaged is shifted from the left eye to the right eye. Comparing the time range in which the left eye is imaged with the time range in which the right eye is imaged, it can be seen that the focus level is calculated to be larger on average in the frame of the right eye portion than in the frame of the left eye portion.

Here, when only a frame having a higher focus level is extracted from all of the plurality of frames constituting the video data, a situation occurs in which the frame of the right eye is included in the frames to be extracted, but the frame of the left eye is not included in the frames to be extracted. In order to include the frame of the left eye in the frames to be extracted, the plurality of frames constituting the video data is sequentially focused in chronological order, and when there is a frame having a focus level smaller than that of a frame of interest within a predetermined time (for example, one second) from the frame of interest, this frame is excluded from the frames to be extracted. This increases the possibility that the frame of the left eye as well as the frame of the right eye remains as the frame to be extracted. It is also possible to suppress an increase in the total volume of the extraction still image data to be recorded.

The example of processing of extracting the extraction still image data from the candidate frame by the image processing device 220 has been described above.

As described above, the image processing program according to the present invention for causing the computer (for example, the image processing device 220) to implement various functions can cause the computer to implement as: the video data acquiring unit 221 that acquires video data to be processed; the focus level calculating unit 222 that calculates focus levels of some or all of the frames constituting the video data; the still image extracting unit 223 that extracts, as extraction still image data, some or all of the frames having focus levels that are equal to or greater than a predetermined value among the frames whose focus levels have been calculated; and the recording unit 226 that records the extraction still image data in a recording means included in the computer. Therefore, it is possible to automatically extract and record the still image data from the video data.

[Supplementary Matter]

In the description of the first embodiment described above, at least the following invention is described so that a person having ordinary knowledge in the field to which the invention belongs can implement the invention.

[1]

A medical program for implementing various kinds of processing in a terminal device used together with a medical examination device including an imaging camera, the medical program implementing:

- a reception function of receiving various types of data including video data (hereinafter referred to as real-time video data) that is captured and simultaneously transmitted in real time by the medical examination device;
- a display control function of playing a video live and displaying the video on a display unit included in the terminal device, the video being indicated by the real-time video data that has been received;
- a video recording function of controlling start/stop of recording of the real-time video data that is currently played live on the basis of a predetermined operation on the terminal device; and
- a recording control function of recording the real-time video data during a period from when recording is started to when the recording is stopped by the video recording function into a recording means included in the terminal device as recorded video data.

[2]

The medical program described in [1], wherein

- the display control function implements a function of displaying a first button for instructing the start/stop of the recording of the real-time video data that is currently played live on the display unit that is a touch panel included in the terminal device, and
- the video recording function implements a function of controlling the start/stop of the recording of the real-time video data that is currently played live on the basis of an input operation on the first button.

[3]

The medical program described in [1] or [2], wherein

- the reception function implements a function of receiving, from the medical examination device, information indicating a control request for the start/stop of the recording of the real-time video data based on an operation on a predetermined operation unit physically provided in the medical examination device, and
- the video recording function implements a function of controlling the start/stop of the recording of the real-time video data that is currently played live on the basis of the information indicating the control request received from the medical examination device.

[4]

The medical program described in any one of [1] to [3], wherein

- the display control function implements a function of displaying, on the display unit, a second button for accepting an input operation of inputting an extraction request for extracting still image data from the recorded video data when the recorded video data is played to display a video on the display unit, and
- the recording control function implements a function of recording still image data corresponding to a still image displayed on the display unit in the recording means when the input operation on the second button is performed.

[5]

The medical program described in any one of [1] to [4], further implementing an acceptance function of accepting an input operation of inputting identification information for identifying an object for examination, wherein

- the recording control function implements a function of recording the real-time video data in the recording means as the recorded video data only when the input operation of inputting the identification information is accepted.

[6]

The medical program described in [5], wherein the recording control function implements a function of recording the real-time video data in the recording means as the recorded video data in association with the identification information input by the input operation that has been accepted.

[7]

The medical program described in any one of [1] to [6], further implementing an acceptance function of accepting an input operation of inputting identification information for identifying an object for examination, wherein the display control function implements a function of playing the video live and displaying the video on the display unit only when the input operation of inputting the identification information is accepted, the video being indicated by the real-time video data that has been received.

[8]

The medical program described in [7], wherein the display control function implements a function of, when the video indicated by the real-time video data is displayed, displaying the identification information indicating an object for examination on the display unit along with the video.

[9]

The medical program described in any one of [1] to [8], wherein the medical examination device is used to examine an eye of a subject, the display control function implements a function of displaying, on the display unit, a third button for selecting a left eye or a right eye of the subject as an object for examination, and the recording control function implements a function of recording, in the recording means, the real-time video data as the recorded video data in association with information regarding selection of the left eye or the right eye of the subject on the basis of a selecting operation on the third button.

[10]

The medical program described in [9], wherein the display control function implements a function of, when the video indicated by the recorded video data is displayed, displaying the information regarding selection of the left eye or the right eye of the subject on the display unit in association with the video.

[11]

The medical program described in any one of [1] to [10], further implementing:

a transmission function of transmitting the recorded video data to a predetermined server device; and a communication control function of performing control so that, while one of communication for receiving the real-time video data by the reception function and communication for transmitting the recorded video data by the transmission function is performed, another communication is inhibited.

[12]

The medical program described in any one of [1] to [11], wherein the display control function enables, when the recorded video data is played to display a video on the display unit, the video to be displayed with a display range being changed by enlarging/reducing the video, and the recording control function enables the video to be further recorded, the video being displayed with the display range being changed by the display control function.

[13]

The medical program described in [12], wherein the recording control function implements a function of, when an input operation on the second button is performed while the video is displayed with the display range being changed on the basis of the display control function, recording still image data corresponding to the still image with the display range displayed on the display unit in the recording means.

[14]

A medical examination system comprising: a medical examination device provided with an imaging camera; a terminal device; and a server device, wherein the medical examination device transmits video data generated by imaging an object for examination to the terminal device in real time, and the terminal device includes a reception unit that receives various types of data including video data (hereinafter referred to as real-time video data) that is captured and simultaneously transmitted in real time by the medical examination device, a display control unit that plays a video live and displays the video on a display unit included in the terminal device, the video being indicated by the real-time video data that has been received, a video recording unit that controls start/stop of recording of the real-time video data that is currently played live on the basis of a predetermined operation on the terminal device, a recording control unit that records the real-time video data during a period from when recording is started to when the recording is stopped by the video recording unit into a recording means included in the terminal device as recorded video data, and a transmission unit that transmits the recorded video data to the server device.

[15]

The medical examination system described in [14], wherein the server device classifies and manages the recorded video data received from the terminal device on the basis of identification information that is information for identifying the object for examination and that is associated by the terminal device.

[16]

The medical examination system described in [14] or [15], wherein the medical examination device functions as one access point, and disables communication connection with another device when establishing communication connection with the terminal device.

In addition, in the description of the second embodiment described above, at least the following invention is described so that a person having ordinary knowledge in the field to which the invention belongs can implement the invention.

[17]

An image processing program for causing a computer to implement a function relating to image processing, the program causing the computer to implement:

a video data acquiring function of acquiring video data to be processed;

a focus level calculating function of calculating focus levels of a part of or all of frames constituting the video data;

a still image extracting function of extracting, as extraction still image data, a part of or all of frames (hereinafter referred to as candidate frames) having focus levels equal to or greater than a predetermined value among the frames whose focus levels have been calculated; and a recording function of recording the extraction still image data in a recording means included in the computer.

[18]

The image processing program described in [17], wherein the still image extracting function includes excluding a predetermined number of the candidate frames from frames to be extracted in descending order of the focus level, when the candidate frames are arranged in chronological order and there is a plurality of the candidate frames within a preset time range.

[19]

The image processing program described in [18], wherein the still image extracting function includes, when there is the candidate frame having the focus level smaller than that of a frame of interest within the predetermined time range from a time point of the frame of interest while the candidate frames are sequentially focused in chronological order during extraction of the extraction still image data from the candidate frames, excluding the candidate frame from the frames to be extracted.

[20]

The image processing program described in any one of [17] to [19], wherein the still image extracting function includes excluding a frame having the focus level that is minimum among the candidate frames from frames to be extracted so that a total number of the extraction still image data does not exceed a predetermined upper limit number, when the extraction still image data is extracted from the candidate frames.

[21]

The image processing program described in any one of [17] to [20], wherein the calculation of the focus level by the focus level calculating function is achieved by edge extraction image generating processing for generating an edge extraction image by execution of edge extraction processing on the frame, and calculation processing of calculating the focus level of a frame corresponding to the edge extraction image on the basis of edge distribution in the edge extraction image.

[22]

The image processing program described in any one of [17] to [21], wherein the focus level calculating function includes executing green component image generating processing of extracting a green component from color information of each pixel constituting the frame to generate green component image data, executing grayscale processing of converting the green component image data into grayscale to generate grayscale image data, and calculating the focus level on the basis of the grayscale image data obtained by the grayscale processing.

[23]

The image processing program described in [22], wherein the focus level calculating function includes executing adjustment processing of adjusting a black level of the grayscale image data, and calculating the focus level on the basis of the grayscale image data which has been adjusted in black level by the adjustment processing.

[24]

The image processing program described in any one of [17] to [23], wherein the focus level calculating function includes setting one frame as a target frame whose focus level is to be calculated among the frames constituting the video data at predetermined time intervals or every predetermined number of frames.

[25]

The image processing program described in any one of [17] to [23], wherein the video data is data of a video obtained by imaging an eye of a subject, and the focus level calculating function includes calculating the focus level of a region obtained by excluding a region of a predetermined range on an upper side and/or a lower side of the frame.

[26]

The image processing program described in any one of [17] to [25], wherein the video data acquiring function includes storing the video data that has been acquired in a storage means included in the computer, the program causing the computer to implement a deleting function of deleting the video data that has been stored in the storage means at a predetermined timing after the extraction still image data is extracted by the still image extracting function.

[27]

The image processing program described in any one of [17] to [26], the program causing the computer to implement:

a display control function of displaying an extraction still image indicated by the extraction still image data on a display unit included in the computer; and an acceptance function of accepting, from a user, a selecting operation on the extraction still image that has been displayed, wherein the recording function implements a function of recording, in the recording means, the extraction still image data that indicates the extraction still image selected by the selecting operation that has been accepted.

[28]

The image processing program described in [27], wherein the display control function implements a function of displaying a video indicated by the video data including the extraction still image on the display unit when a predetermined first input operation is performed, the acceptance function implements a function of accepting a selecting operation of selecting the frame of the video being displayed, and the recording function implements a function of recording, in the recording means, still image data indicating the frame selected by the selecting operation which has been accepted.

[29]

The image processing program described in [28], wherein the display control function includes continuing to play the video data from the extraction still image data when a predetermined second input operation is performed on any of extraction still images indicated by the extraction still image data.

REFERENCE SIGNS LIST

100 medical examination system
110 medical examination device
120 terminal device
121 reception unit
122 display control unit
123 video recording unit
124 recording control unit
125 acceptance unit
126 transmission unit
127 communication control unit
130 server device
210 medical examination device
220 image processing device
221 video data acquiring unit
222 focus level calculating unit
223 still image extracting unit
224 display control unit
225 acceptance unit
226 recording unit
227 deletion unit
230 server device

The invention claimed is:

1. A non-transitory computer-readable medium storing thereon a medical program for implementing various kinds of processing in a terminal device used together with a medical examination device including an imaging camera, the medical program, when executed, causing a processor of the terminal device to perform:

receiving various types of data including real-time video data that is captured and simultaneously transmitted in real time by the medical examination device;

playing a video live and displaying the video on a display unit included in the terminal device, the video being indicated by the real-time video data that has been received;

controlling start/stop of recording of the real-time video data that is currently played live based on a predetermined operation on the terminal device; and recording the real-time video data during a period from when recording is started to when the recording is stopped as recorded video data, wherein the program, when executed, further causes the processor of the terminal device to perform:

calculating focus levels of a part of or all of frames constituting the recorded video data;

extracting, as extraction still image data, a part of or all of candidate frames having focus levels equal to or greater than a predetermined value among the frames whose focus levels have been calculated; and recording the extraction still image data.

2. The non-transitory computer-recording medium according to claim 1, wherein the program, when executed, further causes the processor of the terminal device to perform:

displaying a first button for instructing the start/stop of the recording of the real-time video data that is currently played live on the display unit that is a touch panel included in the terminal device; and controlling the start/stop of the recording of the real-time video data that is currently played live based on an input operation on the first button.

3. The non-transitory computer-recording medium according to claim 1, wherein the program, when executed, further causes the processor of the terminal device to perform:

receiving, from the medical examination device, information indicating a control request for the start/stop of the recording of the real-time video data based on an operation on a predetermined operation unit physically provided in the medical examination device; and controlling the start/stop of the recording of the real-time video data that is currently played live based on the information indicating the control request received from the medical examination device.

4. The non-transitory computer-recording medium according to claim 1, wherein the program, when executed, further causes the processor of the terminal device to perform:

displaying, on the display unit, a second button for accepting an input operation of inputting an extraction request for extracting still image data from the recorded video data when the recorded video data is played to display a video on the display unit; and recording still image data corresponding to a still image displayed on the display unit when the input operation on the second button is performed.

5. The non-transitory computer-recording medium according to claim 1, wherein the program, when executed, further causes the processor of the terminal device to perform:

accepting an input operation of inputting identification information for identifying an object for examination; and recording the real-time video data as the recorded video data only when the input operation of inputting the identification information is accepted.

6. The non-transitory computer-recording medium according to claim 1, wherein the program, when executed, further causes the processor of the terminal device to perform:

accepting an input operation of inputting identification information for identifying an object for examination; and playing the video live and displaying the video on the display unit only when the input operation of inputting the identification information is accepted, the video being indicated by the real-time video data that has been received.

7. The non-transitory computer-recording medium according to claim 1, wherein the medical examination device is used to examine an eye of a subject, and the program, when executed, further causes the processor of the terminal device to perform:

displaying, on the display unit, a third button for selecting a left eye or a right eye of the subject as an object for examination; and recording the real-time video data as the recorded video data in association with information regarding selection of the left eye or the right eye of the subject based on a selecting operation on the third button.

8. The non-transitory computer-recording medium according to claim 1, wherein the program, when executed, further causes the processor of the terminal device to perform excluding a predetermined number of the candidate frames from frames to be extracted in descending order of the focus level, when the candidate frames are arranged in chronological order and there is a plurality of the candidate frames within a preset time range.

9. The non-transitory computer-recording medium according to claim 1, wherein the program, when executed, further causes the processor of the terminal device to perform excluding a frame having the focus level that is minimum among the candidate frames from frames to be extracted so that a total number of the extraction still image data does not exceed a predetermined upper limit number, when the extraction still image data is extracted from the candidate frames.

10. A non-transitory computer-readable medium storing thereon a medical program for implementing various kinds of processing in a terminal device used together with a medical examination device including an imaging camera, the medical program, when executed, causing a processor of the terminal device to perform:

receiving various types of data including real-time video data that is captured and simultaneously transmitted in real time by the medical examination device;

playing a video live and displaying the video on a display unit included in the terminal device, the video being indicated by the real-time video data that has been received;

controlling start/stop of recording of the real-time video data that is currently played live based on a predetermined operation on the terminal device; and recording the real-time video data during a period from when recording is started to when the recording is stopped as recorded video data, wherein the program, when executed, further causes the processor of the terminal device to perform:

transmitting the recorded video data to a predetermined server device; and performing control so that, while one of communication for receiving the real-time video data and communication for transmitting the recorded video data is performed, another communication is inhibited.

11. The non-transitory computer-recording medium according to claim 10, wherein the program, when executed, further causes the processor of the terminal device to perform:

displaying a first button for instructing the start/stop of the recording of the real-time video data that is currently played live on the display unit that is a touch panel included in the terminal device; and controlling the start/stop of the recording of the real-time video data that is currently played live based on an input operation on the first button.

12. The non-transitory computer-recording medium according to claim 10, wherein the program, when executed, further causes the processor of the terminal device to perform:

receiving, from the medical examination device, information indicating a control request for the start/stop of the recording of the real-time video data based on an operation on a predetermined operation unit physically provided in the medical examination device; and controlling the start/stop of the recording of the real-time video data that is currently played live based on the information indicating the control request received from the medical examination device.

13. The non-transitory computer-recording medium according to claim 10, wherein the program, when executed, further causes the processor of the terminal device to perform:

displaying, on the display unit, a second button for accepting an input operation of inputting an extraction request for extracting still image data from the recorded video data when the recorded video data is played to display a video on the display unit; and recording still image data corresponding to a still image displayed on the display unit when the input operation on the second button is performed.

14. The non-transitory computer-recording medium according to claim 10, wherein the program, when executed, further causes the processor of the terminal device to perform:

accepting an input operation of inputting identification information for identifying an object for examination; and recording the real-time video data as the recorded video data only when the input operation of inputting the identification information is accepted.

15. The non-transitory computer-recording medium according to claim 10, wherein the program, when executed, further causes the processor of the terminal device to perform:

accepting an input operation of inputting identification information for identifying an object for examination; and playing the video live and displaying the video on the display unit only when the input operation of inputting the identification information is accepted, the video being indicated by the real-time video data that has been received.

16. The non-transitory computer-recording medium according to claim 10, wherein the medical examination device is used to examine an eye of a subject, and the program, when executed, further causes the processor of the terminal device to perform:

displaying, on the display unit, a third button for selecting a left eye or a right eye of the subject as an object for examination; and recording the real-time video data as the recorded video data in association with information regarding selection of the left eye or the right eye of the subject based on a selecting operation on the third button.

17. A non-transitory computer-readable medium storing thereon a medical program for implementing various kinds of processing in a terminal device used together with a medical examination device including an imaging camera, the medical program, when executed, causing a processor of the terminal device to perform:

receiving various types of data including real-time video data that is captured and simultaneously transmitted in real time by the medical examination device;

playing a video live and displaying the video on a display unit included in the terminal device, the video being indicated by the real-time video data that has been received;

controlling start/stop of recording of the real-time video data that is currently played live based on a predetermined operation on the terminal device; and recording the real-time video data during a period from when recording is started to when the recording is stopped as recorded video data, wherein the program, when executed, further causes the processor of the terminal device to perform:

enabling, when the recorded video data is played to display a video on the display unit, the video to be displayed with a display range being changed by enlarging/reducing the video; and enabling the video to be further recorded, the video being displayed with the display range being changed.

18. The non-transitory computer-recording medium according to claim 17, wherein the program, when executed, further causes the processor of the terminal device to perform:

displaying a first button for instructing the start/stop of the recording of the real-time video data that is currently played live on the display unit that is a touch panel included in the terminal device; and controlling the start/stop of the recording of the real-time video data that is currently played live based on an input operation on the first button.

19. The non-transitory computer-recording medium according to claim 17, wherein the program, when executed, further causes the processor of the terminal device to perform:

receiving, from the medical examination device, information indicating a control request for the start/stop of the recording of the real-time video data based on an operation on a predetermined operation unit physically provided in the medical examination device; and controlling the start/stop of the recording of the real-time video data that is currently played live based on the information indicating the control request received from the medical examination device.

20. The non-transitory computer-recording medium according to claim 17, wherein the program, when executed, further causes the processor of the terminal device to perform:

displaying, on the display unit, a second button for accepting an input operation of inputting an extraction request for extracting still image data from the recorded video data when the recorded video data is played to display a video on the display unit; and recording still image data corresponding to a still image displayed on the display unit when the input operation on the second button is performed.

* * * * *